US010086052B2

(12) United States Patent
Ny et al.

(10) Patent No.: US 10,086,052 B2
(45) Date of Patent: *Oct. 2, 2018

(54) DRUG TARGET FOR PREVENTING AND TREATING PERIODONTAL DISEASE, IMPROVING HEALING OF PERIODONTAL WOUNDS AND PROMOTING ORAL HEALTH

(71) Applicant: Omnio Healer AB, Umeå (SE)

(72) Inventors: Tor Ny, Umeå (SE); Jinan Li, Stockholm (SE); Yongzhi Guo, Umeå (SE); Tomas Lindh, Umeå (SE)

(73) Assignee: Omnio Healer AB, Umeå (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/921,758

(22) Filed: Oct. 23, 2015

(65) Prior Publication Data

US 2016/0184411 A1 Jun. 30, 2016

Related U.S. Application Data

(63) Continuation of application No. 12/439,516, filed as application No. PCT/SE2007/050586 on Aug. 28, 2007.

(60) Provisional application No. 60/944,111, filed on Jun. 15, 2007, provisional application No. 60/823,665, filed on Aug. 28, 2006.

(51) Int. Cl.
*A61K 38/48* (2006.01)
*A61K 8/66* (2006.01)
*A61K 9/00* (2006.01)
*A61Q 11/00* (2006.01)

(52) U.S. Cl.
CPC ............ *A61K 38/484* (2013.01); *A61K 8/66* (2013.01); *A61K 9/0053* (2013.01); *A61Q 11/00* (2013.01); *C12Y 304/21007* (2013.01)

(58) Field of Classification Search
None
See application file for complete search history.

(56) References Cited

U.S. PATENT DOCUMENTS

| | | | |
|---|---|---|---|
| 3,023,143 | A | 2/1962 | Ablondi et al. |
| 5,397,578 | A | 3/1995 | Lazarev et al. |
| 5,716,645 | A | 2/1998 | Tse et al. |
| 6,054,122 | A | 4/2000 | MacPhee et al. |
| 6,656,496 | B1 | 12/2003 | Kilpadi et al. |
| 6,867,342 | B2 | 3/2005 | Johnston et al. |
| 8,318,661 | B2 | 11/2012 | Ny et al. |
| 2003/0026794 | A1 | 2/2003 | Fein |

FOREIGN PATENT DOCUMENTS

| | | |
|---|---|---|
| CN | 1420126 A | 5/2003 |
| CN | 1768138 A | 5/2006 |
| EP | 0480906 A2 | 4/1992 |
| JP | 2003-513682 A | 4/2003 |
| WO | 2000/004941 A1 | 2/2000 |
| WO | 2003/020297 A2 | 3/2003 |
| WO | 2003/045466 A2 | 6/2003 |
| WO | 2003/066842 A2 | 8/2003 |

OTHER PUBLICATIONS

Novel Drug and Treatment, vol. 50, No. 5, 2000, pp. 19-21.
"Merk Manual Home Health Handbook Online", Periodontal Diseases, available online at <http://www.merckmanuals.com/home/print/mouth_and_dental_disorders/periodontal_diseases/gingivitis.html>, accessed on Feb. 24, 2012, 6 pages.
"Plasminogen (PG) and Plasmin (PM)", Nippon Rinsho, vol. 62, Suppl. 12, 2004, pp. 697-699.
"Periodontal Disease—Causes", University of Maryland Medical Center, available online at <http://www.umm.edu/patiented/articles/what_causes_periodontal_disease_000024_3.html>, accessed on Feb. 24, 2012, 4 pages.
Extended European Search Report received for European Patent Application No. 07794195.3, dated Dec. 28, 2011, 7 pages.
Extended European Search Report received for European Patent Application No. 07794196.1, dated Dec. 28, 2011, 7 pages.
Office Action received for Korean Patent Application No. 10-2009-7005738, dated May 20, 2014, 10 pages.
Final Office Action received for U.S. Appl. No. 12/439,516 dated Apr. 23, 2015, 14 pages.
Final Office Action received for U.S. Appl. No. 12/439,516, dated Oct. 17, 2012, 12 pages.
Non Final Office Action Received for U.S. Appl. No. 12/439,516, dated Mar. 7, 2012, 09 pages.
Restriction Requirement received for U.S. Appl. No. 12/439,516, dated Nov. 14, 2011, 7 pages.
Notice of Allowance received for U.S. Appl. No. 12/439,517 dated Apr. 13, 2012, 09 pages.
Non-Final Office Action received for U.S. Appl. No. 13/685,466, dated Dec. 11, 2014, 23 pages.
Office Action Received for Indian Patent Application No. 1906/DELNP/2009, dated Jul. 28, 2014, 2 pages.
Office Action Received for Indian Patent Application No. 1907/DELNP/2009, dated Aug. 1, 2014, 2 pages.
Office Action received for Australian Patent Application No. 2007290881, dated Feb. 21, 2012, 3 pages.
Office Action received for Australian Patent Application No. 2007290882, dated Feb. 8, 2012, 2 pages.
Office Action received for Chinese Patent Application No. 200780032092.X, dated May 31, 2011, 17 pages.

(Continued)

Primary Examiner — Thane Underdahl
(74) Attorney, Agent, or Firm — Morrison and Foerster LLP

(57) ABSTRACT

The present invention relates to the use of a component of the plasminogen-activating pathway and use of compounds which have the capacity to activate plasminogen directly or via the plasminogen-activating pathway, for prophylaxis, prevention and treatment of periodontal disease including peri-implantitis, healing of periodontal wounds and prompting oral health in human and non-human subjects.

32 Claims, 13 Drawing Sheets

(56) References Cited

OTHER PUBLICATIONS

Figure 1:
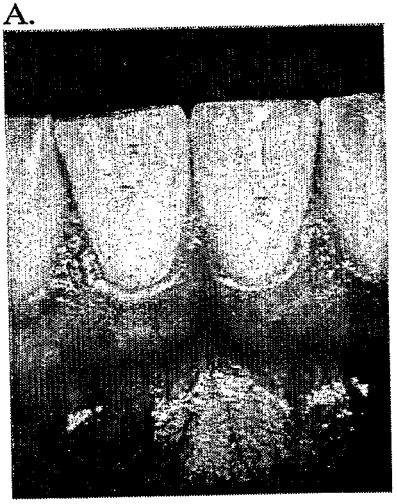
Figure 1:
Figure 1:
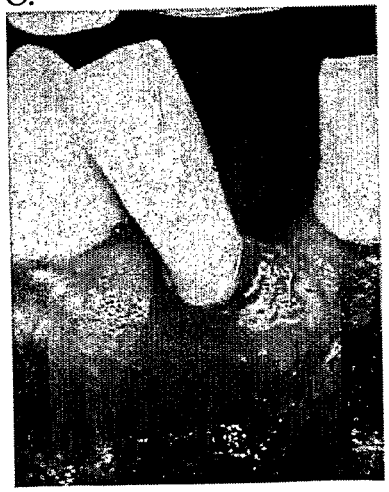

Office Action received for Chinese Patent Application No. 200780032092.X, dated May 25, 2012, 18 pages.
Office Action received for Chinese Patent Application No. 200780032405.1, dated Jul. 27, 2011, 11 pages.
Office Action received for Chinese Patent Application No. 200780032405.1, dated Mar. 27, 2012, 11 pages.
Office Action received for Japanese Patent Application No. 2009-526572, dated Aug. 6, 2013, 7 pages.
Office Action received for Japanese Patent Application No. 2009-526573, dated Sep. 4, 2012, 8 pages.
Office Action received for Eurasian Patent Application No. 200970233, dated Oct. 29, 2010, 4 pages.
Notification of Readiness to Grant the Eurasian Patent received for Eurasian Patent Application No. 200970233/13, dated Mar. 28, 2011, 3 pages.
Office Action received for Canadian Patent Application No. 2662083, dated Jul. 5, 2013, 5 pages.
Office Action received for Canadian Patent Application No. 2662101, dated Jul. 17, 2013, 7 pages.
Aderem A., "Phagocytosis and the Inflammatory Response", The Journal of Infectious Diseases vol. 187, (Suppl 2), 2003, pp. S340-S345.
Alexander et al., "Extracellular Matrix Degradation", Chapter 8 in Cell Biology of Extracellular Matrix, 2nd Edition, 1991, pp. 255-302.
Alexander et al., "Proteinases and Extracellular Matrix Remodeling", Current Opinion in Cell Biology, vol. 1, 1989, pp. 974-982.
American Diabetes Association., "Standards of Medical Care for Patients with Diabetes Mellitus", Diabetes Care, vol. 26, Supplement 1, Jan. 2003, S33-S50.
Andreasen et al., "The Urokinase-Type Plasminogen Activator System in Cancer Metastasis: A Review", International Journal of Cancer, vol. 72, 1997, pp. 1-22.
Berge et al., "PAM, a Novel Plasminogen-Binding Protein from *Streptococcus pyogenes*", The Journal of Biological Chemistry, vol. 268, No. 34, Dec. 5, 1993, pp. 25417-25424.
Brandtzaeg et al., "Plasminogen Activator Inhibitor 1 and 2, Alpha-2-Antiplasmin, Plasminogen, and Endotoxin Levels in Systemic Meningococcal Disease", Thrombosis Research, vol. 57, 1990, pp. 271-278.
Broder et al., "Isolation of a Prokaryotic Plasmin Receptor Relationship to a Plasminogen Activator Produced by the Same Micro-Organism", The Journal of Biological Chemistry, vol. 266, No. 8, Mar. 15, 1991, pp. 4922-4928.
Carmeliet et al., "Physiological Consequences of Loss of Plasminogen Activator Gene Function in Mice", Nature, vol. 368, Mar. 31, 1994, pp. 419-424.
Chertov et al., "Leukocyte Granule Proteins Mobilize Innate Host Defenses and Adaptive Immune Responses", Immunological Reviews, vol. 177, 2000, pp. 68-78.
Clark et al., "Mechanisms of Initiation and Progression of Periodontal Disease", Periodontology, 2000, vol. 2, 1993, pp. 72-82.
Clercq, Erik D., "Antiviral Drugs: Current State of the Art", Journal of Clinical Virology, vol. 22, 2001, pp. 73-89.
Collen et al., "Basic and Clinical Aspects of Fibrinolysis and Thrombolysis", Blood, vol. 78, No. 12, Dec. 15, 1991, pp. 3114-3124.
Collen D., "Ham-Wasserman Lecture: Role of the Plasminogen System in Fibrin-Homeostasis and Tissue Remodeling", Hematology, 2001, pp. 1-9.
Cowan et al., "Diagnostic Tables for the Common Medical Bacteria", The Journal of Hygiene, vol. 59, 1961, pp. 357-372.
Drew et al., "Ligneous Conjunctivitis in Plasminogen-Deficient Mice", Blood, vol .91, No. 5, Mar. 1, 1998, pp. 1616-1624.
Eriksson et al., "First Forty-Eight Hours of Developing Otitis Media: An Experimental Study", The Annals of Otology, Rhinology, and Laryngology, vol. 112, 2003, pp. 558-566.
Eriksson et al., "Spontaneous Development of Otitis Media in Plasminogen-Deficient Mice", International Journal of Medical Microbiology, vol. 296, 2006, pp. 501-509.
Fuchs et al., "Borrelia Burgdorferi Induces Secretion of Pro-Urokinase-Type Plasminogen Activator by Human Monocytes", Infection and Immunity, vol. 64, No. 10, Oct. 1996, pp. 4307-4312.
Gjertsson et al., "Interleukin-10 Ameliorates the Outcome of *Staphylococcus aureus* Arthritis by Promoting Bacterial Clearance", Clinical and Experimental Immunology, vol. 130, 2002, pp. 409-414.
Gouguen et al., "Role of the Pleiotropic Effects of Plasminogen Deficiency in Infection Experiments with Plasminogen-Deficient Mice", Methods, vol. 21, 2000, pp. 179-183.
Guo et al., "Beneficial and Detrimental Effects of Plasmin(ogen) during Infection and Sepsis in Mice", PLoS ONE, vol. 6, No. 9, Sep. 2011, pp. 1-9.
Guo et al., "Protective Effects of Plasmin(ogen) in a Mouse Model of *Staphylococcus aureus*-Induced Arthritis", Arthritis & Rheumatism, vol. 58, No. 3, Mar. 2008, pp. 764-772.
Harrington D J., "Bacterial Collagenases and Collagen-Degrading Enzymes and Their Potential Role in Human Disease", Infection and Immunity, vol. 64, No. 6, Jun. 1996, pp. 1885-1891.
Hauschildt et al., "Bacterial Stimulators of Macrophages", International Review of Cytology, vol. 161, 1995, pp. 263-331.
He et al., "Tissue Cooperation in a Proteolytic Cascade Activating Human Interstitial Collagenase", Proceedings of the National Academy of Sciences of the United States of America, vol. 86, Apr. 1989, pp. 2632-2636.
Jin et al., "Urokinase-Type Plasminogen Activator, an Endogenous Antibiotic", The Journal of Infectious Diseases, vol. 192, Aug. 1, 2005, pp. 429-437.
Kimura et al., "Induction of Experimental Periodontitis in Mice with Porphyromonas Gingivalis-Adhered Ligatures", Journal of Periodontology, vol. 71, No. 7, Jul. 2000, pp. 1167-1173.
Klemm et al., "Fimbriae-Assisted Bacterial Surface Display of Heterologous Peptides", International Journal of Medical Microbiology, vol. 290, 2000, pp. 215-221.
Koutsu et al., "Administration of Fibrinolysin and an Antibiotic in Periodontal Pockets", Journal of the Osaka Odontological Society, vol. 62, No. 4, English abstract on p. 211, Dec. 1999, pp. 201-211.
Lahteenmaki et al., "Bacterial Plasminogen Activators and Receptors", FEMS Microbiology Reviews, vol. 25, 2001, pp. 531-552.
Lahteenmaki et al., "Immobilization of Plasminogen on *Escherichia coli* Flagella", FEMS Microbiology Letters, vol. 106, 1993, pp. 309-314.
Levi et al., "Two-Way Interactions Between Inflammation and Coagulation", Trends in Cardiovascular Medicine, vol. 15, No. 7, 2005, pp. 254-259.
Levy et al., "Antibacterial Resistance Worldwide: Causes, Challenges and Responses", Nature Medicine Supplement, vol. 10, No. 12, Dec. 2004, pp. S122-S129.
Li J., "Multifunctional Roles of Plasmin in Inflammation: Studies of Animal Models on Rheumatoid Arthritis, Multiple Sclerosis, Wound Healing and Infection", Doctoral Thesis, Department of Medical Biochemistry and Biophysics, Feb. 2005, p. 51.
Liakoni et al., "Bacterial Penetration of Pocket Soft Tissues in Chronic Adult and Juvenile Periodontitis Cases An Ultrastructural Study", Journal of Clinical Periodontology, vol. 14, 1987, pp. 22-28.
Liu et al., "Staphylococcal Peptidoglycans Induce Arthritis", Arthritis Research, vol. 3, No. 6, 2001, pp. 375-380.
Mignatti et al., "Biology and Biochemistry of Proteinases in Tumor Invasion", Physiological Reviews, vol. 73, No. 1, Jan. 1993, pp. 161-195.
Ny et al., "Ovulation in Plasminogen-Deficient Mice", Endocrinology, vol. 140, No. 11, 1999, pp. 5030-5035.
Ogura et al., "IL-1ß Increases uPA and uPA Receptor Expression in Human Gingival Fibroblasts", Research Communication, IUBMB Life, vol. 51, 2001, pp. 381-385.
Pancholi et al., "α-Enolase, a Novel Strong Plasmin(ogen) Binding Protein on the Surface of Pathogenic Streptococci", The Journal of Biological Chemistry, vol. 273, No. 23, Jun. 5, 1998, pp. 14503-14515.

(56) References Cited

OTHER PUBLICATIONS

Paul et al., "Matrix Metalloproteinases Contribute to the Blood-Brain Barrier Disruption During Bacterial Meningitis", Annals of Neurology, vol. 44, 1998, pp. 592-600.
International Preliminary Report on Patentability received for PCT Patent Application No. PCT/SE2007/050585, dated Dec. 12, 2008, 10 pages.
International Search Report received for PCT Patent Application No. PCT/SE2007/050585, dated Mar. 19, 2008, 10 pages.
Written Opinion received for PCT Patent Application No. PCT/SE2007/050585 dated Mar. 19, 2008, 16 pages.
International Preliminary Report on Patentability received for PCT Patent Application No. PCT/SE2007/050586, dated Dec. 12, 2008, 10 pages.
International Search Report received for PCT Patent Application No. PCT/SE2007/050586, dated Mar. 19, 2008, 9 pages.
International Written Opinion received for PCT Patent Application No. PCT/SE2007/050586, dated Sep. 3, 2008, 16 pages.
Ploplis et al., "Effects of Disruption of the Plasminogen Gene on Thrombosis, Growth, and Health in Mice", Circulation, vol. 92, No. 9, 1995, pp. 2585-2593.
Qasimi et al., "Divergent Mechanisms Utilized by SOCS3 to Mediate Interleukin-10 Inhibition of Tumor Necrosis Factor α and Nitric Oxide Production by Macrophages", The Journal of Biological Chemistry, vol. 281, No. 10, Mar. 10, 2006, pp. 6316-6324.
Raaphorst et al., "Early Inhibition of Activated Fibrinolysis Predicts Microbial Infection, Shock and Mortality in Febrile Medical Patients", Thrombosis and Haemostatis, vol. 86, 2001, pp. 543-549.
Rams et al., "Staphylococci in Human Periodontal Diseases", Oral Microbiology and Immunology, vol. 5, 1990, pp. 29-32.
Raum et al., "Synthesis of Human Plasminogen by the Liver", Science, vol. 208, May 30, 1980, pp. 1036-1037.
Rifkin et al., "Growth Factor Control of Extracellular Proteolysis", Cell Differentiation and Development, vol. 32, 1990, pp. 313-318.
Rifkin et al., "Proteolytic Control of Growth Factor Availability", APMIS, vol. 107, 1999, pp. 80-85.
Ross et al., "Methicillin-Resistant *Staphylococcus aureus* Septic Arthritis: An Emerging Clinical Syndrome", Rheumatology, vol. 44, 2005, pp. 1197-1198.
Saksela et al., "Cell-Associated Plasminogen Activation: Regulation and Physiological Functions", Annual Review of Cell Biology, vol. 4, 1988, pp. 93-126.
Schott et al., "Therapy with a Purified Plasminogen Concentrate in an Infant with Ligneous Conjunctivitis and Homozygous Plasminogen Deficiency", The New England Journal of Medicine, vol. 339, No. 23, Dec. 3, 1998, pp. 1679-1686.
Scully et al., "Oral Lesions Indicative of Plasminogen Deficiency (Hypoplasminogenemia)", Oral Surgery, Oral Medicine, Oral Pathology, Oral Radiology and Endodontics, vol. 91, No. 3, Mar. 2001, pp. 334-337.
Shibata et al., "Antisense Oligonucleotide of Tissue Inhibitor of Metalloproteinase-1 Induces the Plasminogen Activator Activity in Periodontal Ligament Cells", Journal of Periodontology, vol. 70, No. 10, Oct. 1999, pp. 1158-1165.
Sierra David H., "Fibrin Sealant Adhesive Systems: A Review of Their Chemistry, Material Properties and Clinical Applications", Journal of Biomaterials Applications, vol. 7, Apr. 1993, pp. 309-352.
Smith, R L., "Staphylococcal Septic Arthritis: Antibiotic and Nonsteroidal Anti-Inflammatory Drug Treatment in a Rabbit Model", Journal of Orthopaedic Research, vol. 15, 1997, pp. 919-926.
Sottrup et al., "Amino-Acid Sequence of Activation Cleavage Site in Plasminogen: Homology with "Pro" Part of Prothrombin", Proceedings of the National Academy of Sciences of the United States of America, vol. 72, No. 7, Jul. 1975, pp. 2577-2581.
Spier et al., "Local Ambulatory Treatment of Chronic Leg Ulcers with Hyaluronidase, Plasminogen, and Antibiotics", Surgery, Gynecology & Obstetrics, vol. 98, 1954, pp. 667-674.
Sulniute et al., "Plasmin is Essential in Preventing Periodontitis in Mice", The American Journal of Pathology, vol. 179, No. 2, Aug. 2011, pp. 819-828.
Sun et al., "Plasminogen is a Critical Host Pathogenicity Factor for Group a Streptococcal Infection", Science, vol. 305, Aug. 27, 2004, pp. 1283-1286.
Teele et al., "Epidemiology of Otitis Media During the First Seven Years of Life in Children in Greater Boston: A Prospective, Cohort Study", The Journal of Infection Diseases, vol. 160, No. 1, Jul. 1989, pp. 83-94.
Tefs et al., "Molecular and Clinical Spectrum of Type I Plasminogen Deficiency: A Series of 50 Patients", Blood, vol. 108, No. 9, Nov. 1, 2006, pp. 3021-3026.
Tentolouris et al., "Methicillin-Resistant *Staphylococcus aureus*: An Increasing Problem in a Diabetic Foot Clinic", Diabetic Medicine, vol. 16, Sep. 1999, pp. 767-771.
Travis et al., "Control of Coagulation and Fibrinolysis by Plasma Proteinase Inhibitors", Behring Institute of Mitteilungen, vol. 73, 1983, pp. 56-65.
Wallen Per., "Biochemistry of Plasminogen", Fibrinolysis, CRC Press: 1980, pp. 2-25.
Werb et al., "Endogenous Activiation of Latent Collagenase by Rheumatoid Synovial Cells. Evidence for a Role of Plasminogen Activator", The New England Journal of Medicine, vol. 296, No. 18, May 5, 1977, pp. 1017-1023.
Wiman et al., "Structural Relationship Between "Glutamic Acid" and "Lysine" Activation Peptide as Studied by Affinity Chromatography", European Journal of Biochemistry, vol. 50, 1975, pp. 489-494.
Wozniak Gernold, "Fibrin Sealants in Supporting Surgical Techniques: the Importance of Individual Components", Cardiovascular Surgery, vol. 11, No. S1, Aug. 2003, pp. 17-21.
Final Office Action received for U.S. Appl. No. 13/685,466 dated Jul. 9, 2015, 24 pages.
Cederholm, Williams, "Concentration of Plasminogen and Antiplasmin in Plasma and Serum", J Clin Pathol, vol. 34, Apr. 1, 1981, pp. 979-981.
Krebs, H. A., "Chemical Composition of Blood Plasma and Serum", Annual Review of Biochemistry, vol. 19, 1950, pp. 409-430.
Non Final Office Action received for U.S. Appl. No. 14/964,481, dated Jun. 16, 2017, 13 pages.

A.

B.

DRUG TARGET FOR PREVENTING AND TREATING PERIODONTAL DISEASE, IMPROVING HEALING OF PERIODONTAL WOUNDS AND PROMOTING ORAL HEALTH

CROSS-REFERENCE TO RELATED APPLICATIONS

This application is a Continuation of U.S. patent application Ser. No. 12/439,516, claiming an international filing date of Aug. 28, 2007; which is the National Stage of International Patent Application No. PCT/SE2007/050586, filed Aug. 28, 2007; which claims the benefit of U.S. Provisional Patent Application Nos. 60/823,665, filed Aug. 28, 2006, and 60/944,111, filed Jun. 15, 2007; the disclosures of which are herein incorporated by reference in their entirety.

FIELD OF INVENTION

This invention relates to compound and methods for prophylaxis, prevention and/or treatment of infectious periodontal disease e.g. gingivitis and periodontitis, and necrotic conditions affecting the gum tissue, relates to promoting oral health in general, and also relates to improving healing of periodontal wounds such as surgical wounds locally. In particular, the invention relates to a novel method of preventing and treating infectious periodontal disease, promoting oral health and improving healing of periodontal wounds.

BACKGROUND

Periodontal Disease

Periodontal disease is a chronic inflammatory disease that affects the tissues that support and anchor the teeth, also known as the periodontium. It is caused by the imbalanced interplay between the specific subgingival microorganisms and the host immune and inflammatory response (1). It affects nearly three-quarters of the adult populations and is regarded as one of the most common diseases to human being. The tissues that are involved in periodontal diseases are the gums, which include the gingiva, the periodontal ligament, the cementum, and the alveolar bone (FIG. 1). The gingiva is a pink-colored keratinized mucus membrane that covers parts of the teeth and part of the alveolar bone. The periodontal ligament is the main part of the gums. The cementum is a calcified structure that covers the lower parts of the teeth. The alveolar bone is a set of ridges from the jaw bones (maxillary and mandible) in which the teeth are embedded. The area where periodontal disease is initiated is the gingival sulcus, a pocket between the teeth and the gums.

Infection, inflammation and subsequent host defense and wound healing are all hallmarks of periodontal disease. This disease begins as a mixed bacterial infection in the gingiva surrounding teeth (2). In the healthy mouth, more than 500 species of microorganisms have been found. In periodontal diseases, several potential periodontal pathogens have been studied including *Porphyromonas gingivalis, Campylobacter rectus, Actinobacillus actinomcetemcomitans*, and *Fusobacterium nucleatum*, which are considered to represent a significant portion of the pathogenic microbiota. These microorganisms can induce several factors, such as IL-1, IL-6, TNF, as well as enzymes, in host cells which directly or indirectly are thought to cause irreversible tissue destruction including the destruction of the gums, the alveolar bone, the outer layer of the tooth root and eventually leads to tooth loss. Furthermore, serious periodontal disease can lead to bad breath, heart disease and stroke, diabetes, respiratory diseases and premature delivery during pregnancy. There are other pathogenic factors such as smoking/tobacco use, genetics, pregnancy and puberty, stress, medications, diabetes, poor nutrition and other systemic diseases.

Another form of infectious destruction of the alveolar bone, closely resembling periodontitis, namely Periimplantitis, can occur after surgical implantation of an alloplastic material into the jaws. The implantation method is often referred to as osseointegration (3), which entails close contact between the alloplastic material, i.e. the dental implant (often made of titanium), and the living bone. The method is used to restore occlusion subsequent to the loss of natural teeth and is now a standard method for treating edentulism. A principle difference between the osseointegrated dental implant and the natural tooth is the absence of a true periodontium around the implant. While the normal tooth is suspended in a meshwork of collagenous fibers that allows for a physiological mobility of the tooth within the alveolar bone, the dental implant is firmly connected to the bone without intervening soft tissue. Despite this major dissimilarity in attachment to the bone tissue, the pathological changes at teeth and implants during infection share many key features such as infection via biofilm formation and colonization, inflammatory response, as well as immunological defence. Thus, periimplantitis is an inflammatory/infectious process affecting the tissues around an osseointegrated implant in function, resulting in loss of supporting bone. Periimplantitis may lead to complete disintegration and implant loss even if extensive treatment aiming at resolving the periimplant infection has been performed. Periimplantitis also happens as reversible inflammatory/infectious changes of the peri-implant soft tissues without any bone loss. The prevalence of periimplantitis in the soft tissue has been reported in the range of 8-44%, while frequency of periimplantitis in the bone has been reported in the range of 1-19%. The wide ranges for the frequencies seem to be due to differences in defining the entity, at least in part. The frequency of periimplantitis is most likely related to the number of years implants have been worn. Since dental implant treatment was introduced comparatively recently, the numbers will probably increase over the years. Considering the large similarities in the inflammatory response and the immunological defence against infection at teeth and dental implants periimplantitis could be regarded as a form of periodontal disease affecting implanted alloplastic material.

Periodontal disease is an important aspect of general oral health. Oral health refers to the status of health of the oral and related tissues which enables an individual to eat, speak and socialize without active disease, discomfort or embarrassment and which contributes to general well-being. Major indications of oral health include the bacterial flora in the saliva and gum tissue, as well as the tissue necrosis and inflammation in the gum tissue. Oral health is integral to general health and should not be considered in isolation.

Antibiotics and other antimicrobial drugs have been widely used in treatment of infectious diseases since the World War II era. The success of antimicrobials against disease-causing microbes is among modern medicine's great achievements. However, many antimicrobials are not as effective as they used to be. A key factor in the development of antibiotic resistance is the ability of infectious organisms to adapt quickly to new environmental conditions. Over time, some bacteria have developed ways to circumvent the effects of antibiotics. Widespread use of antibiotics is thought to have spurred evolutionarily adaptations that enable bacteria to survive these once so powerful drugs. Ultimately, the increasing difficulty in fighting off microbes leads to an increased risk of acquiring infections in a hospital or other setting. Drug resistance is an especially difficult problem for hospitals harboring critically ill patients who are less able to fight off infections without the help of antibiotics. Therefore, there is an increasing awareness that novel therapeutic strategies are highly needed to improve the infection defense against infection.

Treatment of periodontal disease includes conservative (non-surgical) methods and surgical methods. Conservative treatment consists of deep cleanings known as scaling and rootplaning as well as gingival curettage. This treatment is aimed to remove the biofilm colonizing the affected root surfaces and reestablish an environment where healing can occur. Accompanied with good oral hygiene this will maintain healthy normal gums Surgical periodontal treatment consists of osseous (bone) surgery, gingival/periodontal grafts, gingival flap procedure, frenectomy, gingivectomy, guided tissue regeneration/bone augmentation. However, despite the various therapeutic methods that have successfully improved the treatment of periodontal disease, great challenges in oral health still exist. Such challenging factors include the increasing resistance of oral bacteria against antibiotics, the needs for simpler methods to improve oral health in general, the expensive and tedious dental care procedure, the stressful modern life and the heavier dental burden in under-privileged groups in developed and developing countries. Therefore novel methods of preventing and treating periodontal disease, promoting oral health and improving healing of periodontal wounds are in great needs.

Necrosis

Necrosis is the name given to unprogrammed or accidental death of cells and living tissue. It is less orderly than apoptosis, which are part of programmed cell death. In contrast with apoptosis, cleanup of cell debris by phagocytes of the immune system is generally more difficult, as the disorderly cell death generally does not send "eat-me" cell signals which tell nearby phagocytes to engulf the dying cell. This lack of signaling makes it harder for the immune system to locate and recycle dead cells which have died through necrosis than if the cell had undergone apoptosis. The release of intracellular content after cellular membrane damage is cause of inflammation in necrosis. There are many causes of necrosis including injury, infection, cancer, infarction, invenomation and inflammation. Severe damage to one essential system in the cell leads to secondary damage to other systems, a so-called "cascade of effects". Necrosis is caused by special enzymes that are released by lysosomes which are capable of digesting cell components or the entire cell itself. The injuries received by the cell may compromise the lysosome membrane, or may set off an unorganized chain reaction which causes the release in enzymes. Unlike in apoptosis, cells that die by necrosis may release harmful chemicals that damage other cells. Necrosis of biopsy material is halted by fixation or freezing.

Necrosis occurs in certain types of periodontal disease. Necrotizing gingivitis is an inflammatory destructive gingival condition characterized by interproximal necrotic ulcers, spontaneous bleeding, rapid onset of pain and bad odor. Unless properly treated, necrotizing gingivitis has a marked tendency for recurrence and lead to considerable loss of periodontal support.

Currently there are four major therapeutic methods to cure necrosis. The first is surgical, which is the most rapid, and therefore is recommended when large necrotic areas or thick scars are present. The second is mechanical, which includes hydrotherapy, dextranomers and wound irrigation. The third is enzymatical, the enzyme used is mainly collagenase (eg: Santyl), however, the effect is too slow when infection presents; and the fourth is through autolytic method, which is via enzymes in wound fluid but the effect is extremely slow. However, none of the four treatment methods could give a functional and aesthetically satisfactory necrosis removal and tissue remodeling. Therefore, a novel therapeutic strategy is in great need in order to achieve a successful removal of necrosis.

The Plasminogen-Activation System

Plasmin is the key component of the PA system. It is a broad-spectrum protease which has the ability to degrade several components of the ECM including fibrin, gelatin, fibronectin, laminin and proteoglycans (4). In addition, plasmin can convert some pro-matrix metalloproteinases (pro-MMPs) to active MMPs. It has therefore been suggested that plasmin may be an important upstream regulator of extracellular proteolysis (5;6). Plasmin is formed from the zymogen plasminogen through proteolytic cleavage by either of two physiological PAs, tPA or uPA. As plasminogen is present in plasma and other body fluids at relatively high levels, the regulation of the PA system occurs mainly at the level of synthesis and activity of the PAs. Synthesis of the components of the PA system is highly regulated by different factors such as hormones, growth factors and cytokines. In addition, there exist specific physiological inhibitors of plasmin and PAs. The main inhibitor of plasmin is $\alpha_2$-antiplasmin. The activity of PAs is regulated by PAI-1, which inhibits both uPA and tPA, and PAI-2, which inhibits mainly uPA. Certain cells also have a specific cell-surface receptor for uPA (uPAR) that can direct proteolytic activity to the cell surface (8;9).

Plasminogen is a single-chain glycoprotein consisting of 790 amino acids with a molecular mass of approximately 92 kDa (7;8). Plasminogen is mainly synthesized in the liver and is abundant in most extracellular fluids. In plasma the concentration of plasminogen is approximately 2 µM. Plasminogen therefore constitutes a large potential source of proteolytic activity in tissues and body fluids (9;10). Plasminogen exists in two molecular forms: Glu-plasminogen and Lys-plasminogen. The native secreted and uncleaved form has an amino-terminal (N-terminal) glutamic acid and is therefore designated Glu-plasminogen. However, in the presence of plasmin, Glu-plasminogen is cleaved at $Lys^{76}$-$Lys^{77}$ to become Lys-plasminogen. Compared to Glu-plasminogen, Lys-plasminogen has a higher affinity for fibrin and is activated by PAs at a higher rate. These two forms of plasminogen can be cleaved at the $Arg^{560}$-$Val^{\star}$peptide bond by uPA or tPA, resulting in the formation of the disulphide-linked two-chain protease plasmin (11). The amino-terminal part of plasminogen contains five homologous triple-loops, so-called kringles, and the carboxyl-terminal part contains the protease domain. Some of the kringles contain lysine-binding sites which mediate the specific interaction of plasminogen with fibrin and its inhibitor $\alpha_2$-AP. A novel and interesting finding is that a 38-kDa fragment of plasminogen, consisting of kringles 1-4, is a potent inhibitor of angiogenesis. This fragment is termed angiostatin and can be generated from plasminogen through proteolytic cleavage by several MMPs.

The main substrate for plasmin is fibrin, and dissolution of fibrin is pivotal for prevention of pathological blood clot formation (12). Plasmin also has substrate specificities for several other components of the ECM, including laminin, fibronectin, proteoglycans and gelatin, indicating that plasmin also plays an important role in ECM remodeling (8;13; 14). Indirectly, plasmin can also degrade additional components of the ECM through its ability to convert some pro-MMPs to active MMPs, including MMP-1, MMP-2, MMP-3 and MMP-9. It has therefore been suggested that plasmin may be an important upstream regulator of extracellular proteolysis (15). In addition, plasmin has the ability to activate latent forms of certain growth factors (16-18). In vitro, plasmin also cleaves components of the complement system and thereby release chemotactic complement fragments.

The PA system has been suggested to be involved at several stages and by various mechanisms during bacterial invasion (19). A vast number of pathogens express plasmin (ogen) receptors (20;21). Bacteria also influence the secretion of PAs and their inhibitors from mammalian cells (22;23). For instance, production of uPA has been found to be enhanced in cells infected by various bacteria (24). To date, in vivo evidence for a role of plasminogen activation in pathogenesis exists in a few bacteria such as *Yersinia pestis, Borrelia*, and group A streptococci.

Binding of plasminogen to receptors present on the surfaces of some bacteria convert these bacteria into proteolytic organisms. In Gram-negative bacteria, the filamentous surface appendages form a major group of plasminogen receptors (25;26). In Gram-positive bacteria, surface-bound molecules have been identified as plasminogen receptors (27; 28). As a consequence, plasmin can be generated on the surface of microorganisms such as *Haemophilus influenzae, Salmonella typhimurium, Streptococcus pneumoniae, Yersinia pestis*, and *Borrelia burgdorferi*, which can lead to a degradation of mammalian ECM. Furthermore, bacterial proteases may also directly activate latent pro-collagenases or inactivate protease inhibitors in human plasma, and thus contribute to tissue damage and bacterial spread across tissue barriers (29;30).

Models of Periodontal Disease and Periodontal Wounds

Models of periodontal disease include spontaneous type and induced type. The periodontal tissue is exposed to a microbe-rich environment. Bacterial invasion and subsequent host defense in the oral cavity occurs constantly and normally remain in balance. Disruption of this host-bacterial balance causes various types of periodontal disease. This could be due to an imbalance between the oral microbiota, alterations in phagocyte function and/or specific immune response. Severe periodontal disease occurs in approximately 2% of US adolescents and in approximately 20% of US adults.

Inducing periodontal disease by certain bacterial species provides defined models for periodontitis. Commonly used periodontal pathogens include *Porphyromonus gingivalis, Campylobacter rectus, Actinobacillus actinomycetemcomitans*, and *Fusobacterium nucleatum*, which are considered to represent a significant portion of the pathogenic microbiota. They possess or can induce in host cells several factors, such as IL-1, IL-6, tumor necrosis factor, surface-associated proteins, fimbriae, vesicles, toxins, and enzymes, which are thought to cause, directly or indirectly, irreversible loss of periodontal supportive tissues.

Periodontal wounds are commonly seen, especially during periodontal surgery. Periodontal wound model can be established by inducing incisional wounds at the gum tissue in the mice. Thereafter the healing pattern of the wounds and the effects of the candidate drug or compounds can be evaluated.

Current method for treating infections such as necrosis as well as periodontal disease have drawbacks as discussed above. Thus, there is still a need in the art for improved strategies and means for treating periodontal disease and improving oral health.

SUMMARY OF THE INVENTION

The present invention relates to the novel discovery that components of the plasminogen-activation pathway, and compounds with the capacity to activate plasminogen can be used for new and improved strategies for preventing and treating periodontal disease and tissue necrosis, for healing of periodontal wounds (such as surgical wounds) and for promoting oral health in general. The administration of plasminogen and/or other members of the plasminogen-activation pathway or compounds with the capacity to activate plasminogen play a pluripotent role in protecting against bacterial-induced infection and promoting healing of periodontal wounds by activating inflammatory cells, accelerating migration of keratinocytes, killing bacteria, removing necrotic tissue and enhancing cytokine expression. The extensive occurrence of periodontal disease in plasminogen-deficient mice under natural conditions also provides an excellent animal model to for studying periodontal disease, and screening methods for identifying and evaluating new drugs and treatment methods for various aspects of periodontal disease, periodontal wound improvement and prompt oral health in general.

Accordingly, the present invention provides the use of an active agent or compound that is a component of the plasminogen-activating pathway or has the capacity to activate plasminogen directly or via the plasminogen-activating pathway for the manufacture of a pharmaceutical composition comprising an effective amount of the compound/agent, or a combination of two or more such agents/compounds, for the prophylaxis, prevention and/or treatment of periodontal disease, especially infectious periodontal disease, and/or removal of necrosis in the gum tissue, in a subject in need of such treatment, Preferably, the active agent is selected from plasminogen activators, tPA, uPA, streptokinase, saruplase, alteplase, reteplase, tenecteplase, anistreplase, monteplase, lanoteplase, pamiteplase, staphylokinase and recombinant forms and variants of the components of the plasminogen-activating pathway. More preferably, the active agent is selected from plasmin or plasminogen and their derivatives e.g. kringle domains of plasmin or plasminogen, protein fragments of plasmin or plasminogen, mini-plasminogen and mini-plasmin as well as the synthetic derivatives of plasmin or plasminogen. Most preferably, the active agent is plasminogen and its derivatives. The active agent can be administered by any route of administration known in the art. Preferred, non-limiting, routes of administration include topical application, intra-gingival injection and intravenous injection. The agent may also be present in a wound dressing applied onto the infected area of periodontal tissue, if possible, from which it is transferred to the infected site of periodontal tissue. The composition may be part of a gel, lotion, balm, paste (toothpaste), gargling solution (mouthwash solution) or wound dressing The present invention also provides the use of a compound or active agent that is a component of the plasminogen-activating pathway or a compound which has the capacity to activate plasminogen directly or via the plasminogen-activating pathway for the manufacture of a pharmaceutical composition comprising an effective amount of such compound/agent, or a combination of tow or more such compounds/agents, for improving resolution and/or promoting the healing of periodontal wounds and surgical periodontal wounds, especially infectious periodontal wounds and surgical infectious periodontal wounds in a subject in need of such treatment. Preferably, the active agent is selected from plasminogen activators, tPA, uPA, streptokinase, saruplasc, alteplase, reteplase, tenecteplase, anistreplase, monteplase, lanoteplase, pamiteplase, staphylokinase and recombinant forms and variants of the components of the plasminogen-activating pathway. More preferably, the active agent is selected from plasmin or plasminogen. Most preferably, the active agent is plasminogen. The active agent can be administered by any route of administration known in the art. Preferred, non-limiting, routes of administration include topical application, intra-gingival injection and intravenous injection. The agent may also be present in a wound dressing, a gel, lotion, balm, paste, mouthwash solution and toothpaste applied onto the wounded area of periodontal tissue, if possible, from which it is transferred to the wounded site of periodontal tissue.

Furthermore, the present invention provides a method of prompting oral health, comprising administering a composition comprising an active agent which is a component of the plasminogen-activation pathway or a compound with the capacity to activate plasminogen, or a combination of two or more such agents. Preferably, the active agent is selected from plasminogen activators, tPA, uPA, streptokinase, saruplase, alteplase, reteplase, tenecteplase, anistreplase, monteplase, lanoteplase, pamiteplase, staphylokinase and recombinant forms and variants of the components of the plasminogen-activating pathway. More preferably, the active agent is selected from plasmin or plasminogen. Most preferably, the active agent is plasminogen, such as Glu-plasminogen or Lys-plasminogen. The active agent can be administered by any route of administration known in the art. The composition may be part of a gel, lotion, balm, paste, or dressing. Preferred, non-limiting, routes of administration include topical application such as tooth paste or the usage of gargling solution (mouthwash solution) which can be used for strengthening teeth against decay and prompting oral health.

The invention also provides for a method of initiating the host defense for treating periodontal disease, especially infectious periodontal disease, in conditions where host defense is retarded or impaired, comprising administering an active ingredient which is plasmin or plasminogen. In a particular embodiment, the method of the invention can be used for improving host defense against periodontal disease in conditions of local or systemic deficiency/impairment of plasmin or plasminogen.

In another embodiment, the invention provides a method for prophylaxis, prevention and treatment of periodontal disease, especially infectious periodontal disease, improving healing of periodontal wounds such as surgical wounds and promoting oral health in human or non-human subjects by administering a compound or drug which is plasminogen or plasmin and their derivatives, an activator of plasminogen, or a compound enhancing the activity of plasmin. Preferably, the compound is administered locally to attain a high concentration in the infected area.

Moreover, the invention provides for a method for reducing or preventing oral necrosis formation by administering a composition comprising local or systemic administration of a composition comprising a compound which is a component of the plasminogen activation pathway or compounds with the capacity to activate plasminogen. The composition may be part of a gel, lotion, balm, paste, or wound dressing. Alternatively, the composition may be administered systemically. In one embodiment, the method of the invention is applied in conjunction with plastic surgery in the periodontal tissue to reduce the occurrence and the formation of infection, ulcer and necrosis.

In another embodiment, the invention provides a pharmaceutical composition for the treatment, prophylaxis and prevention of periodontal discasc, especially infectious periodontal discasc, comprising an effective amount of a compound which is a component of the plasminogen-activating pathway or compounds with the capacity to activate plasminogen. The component of the plasminogen-activating pathway can be selected from plasminogen, Lys-plasminogen, Glu-plasminogen, plasmin, kringle domains of plasminogen and plasmin, mini-plasminogen, mini-plasmin, plasminogen activators, tPA, and uPA. Preferably the component of the plasminogen-activating pathway is plasminogen or plasmin. The compounds with the capacity to activate plasminogen can be selected from streptokinase, saruplase, alteplase, reteplase, tenecteplase, anistreplase, monteplase, lanoteplase, pamiteplase, staphylokinase and recombinant forms and variants of the components of the plasminogen-activating pathway.

In a further embodiment, the invention provides a method for prophylaxis, prevention and/or treatment of periodontal disease, especially infectious periodontal disease, comprising administering a pharmaceutical composition comprising an effective amount of a compound according to claims 1-16, which compound is a component of the plasminogen-activating pathway or which has the capacity to activate plasminogen directly or via the plasminogen-activating pathway to a subject in need of such treatment. The component of the plasminogen-activating pathway can be selected from plasminogen, Lys-plasminogen, Glu-plasminogen, plasmin, kringle domains of plasminogen and plasmin, mini-plasminogen, mini-plasmin, plasminogen activators, tPA, and uPA. Preferably the component of the plasminogen-activating pathway is plasminogen or plasmin. The compound with the capacity to activate plasminogen can be selected from streptokinase, saruplase, alteplase, reteplase, tenecteplase, anistreplase, monteplase, lanoteplase, pamiteplase, staphylokinase and recombinant forms and variants of the components of the plasminogen-activating pathway.

In yet another embodiment, the invention provides a pharmaceutical composition for promoting the healing of periodontal wounds, especially infectious periodontal wounds, which comprises an effective amount of a component of the plasminogen-activating pathway or a compound with the capacity to activate plasminogen. The component of the plasminogen-activating pathway can be selected from plasminogen, Lys-plasminogen, Glu-plasminogen, plasmin, kringle domains of plasminogen and plasmin, mini-plasminogen, mini-plasmin, plasminogen activators, tPA, and uPA. Preferably the component of the plasminogen-activating pathway is plasminogen or plasmin. The compound with the capacity to activate plasminogen can be selected from streptokinase, saruplase, alteplase, reteplase, tenecteplase, anistreplase, monteplase, lanoteplase, pamiteplase, staphylokinase and recombinant forms and variants of the components of the plasminogen-activating pathway.

In a further embodiment, the invention provides a method for promoting the healing of periodontal wounds, especially infectious periodontal wounds, comprising administering a pharmaceutical composition comprising an effective amount of compound, which is a component of the plasminogen-activating pathway or which has the capacity to activate plasminogen directly or via the plasminogen-activating pathway to a subject in need of such treatment. The component of the plasminogen-activating pathway can be selected from plasminogen, Lys-plasminogen, Glu-plasminogen, plasmin, kringle domains of plasminogen and plasmin, mini-plasminogen, mini-plasmin, plasminogen activators, tPA, and uPA. Preferably the component of the plasminogen-activating pathway is plasminogen or plasmin. The compound with the capacity to activate plasminogen can be selected from streptokinase, saruplase, alteplase, reteplase, tenecteplase, anistreplase, monteplase, lanoteplase, pamiteplase, staphylokinase and recombinant forms and variants of the components of the plasminogen-activating pathway.

DETAILED DESCRIPTION OF THE INVENTION

Improvement of Preventing and Treating Periodontal Disease, Healing Periodontal Wounds and Maintaining Oral Health According to the invention, providing or enhancing the levels of plasminogen and/or plasmin can be used for prophylaxis, prevention and treatment of periodontal disease, accelerating the healing of periodontal wounds and prompting the oral health. This may be accomplished in many different ways. For instance, by treating a patient with active agents, drugs, hormones, cytokines, antibodies, or other compounds that up-regulate the expression of plasmin, plasminogen, or plasminogen-activators; reduce the degradation of either of these components; the local or systemic levels of plasminogen and/or plasmin can be increased. In another embodiment, local plasmin or plasminogen level is increased by directly applying plasmin/plasminogen proteins and their derivatives. In yet another embodiment, plasmin activity is enhanced by administration of an activator of plasmin or /plasminogen. In further another embodiment, an artificial, a recombinant or a bacterial plasminogen activator such as streptokinase and staphylokinase is used. In further another embodiment, a fragment of plasminogen protein sequence such as synthetic peptides, kringle domains miniplasminogen or miniplasmin is used.

Components of the plasminogen-activation pathway or compounds with the capacity to activate plasminogen may be produced by purifying the component(s) or compounds from bacteria, humans, or other animals, or by recombinant production in yeast such as *S. cerevisiae*, in bacteria such as *E. coli*, and in mammalian cell line such as Chinese Hamster Ovary cell line. The component may be wild-type or modified/mutated. Fragments of the component which retain at least a part of the desired activity of the full-length component may also be used. In a preferred embodiment, a substantially pure preparation of human plasminogen is used. In another preferred embodiment, a substantially pure preparation of human plasmin is used. In further another preferred embodiment, a substantially pure preparation of miniplasminogen, miniplasmin or a fragment of plasminogen protein sequence is used.

Applications

The method of the invention is used for prophylaxis, prevention and treatment of periodontal disease, healing of periodontal wounds and prompting oral health for daily life. Such animals include, but are not limited to, vertebrates such as humans and domestic animals, including dogs, cats, horses, cows, pigs, and domesticated fowls. In one embodiment, the methods of the invention are applied for management of periodontal disease in a human subject. The human or non-human subject may or may not suffer from a condition which impairs the healing of periodontal disease. In another embodiment, the methods of the invention are applied for improving the healing of periodontal wounds. The periodontal wounds include, but are not limited to, traumatic wounds due to injuries and surgical wounds. In a particular embodiment, the subject is a human which plans to undergo, is undergoing, or has undergone, plastic surgery in the periodontal area of the mouth. In such a case, a composition comprising, e.g., plasminogen, can be applied or administered both prior to and/or after surgery. In a further another embodiment, the methods of the invention are applied for prompting oral health. In such a case, a composition comprising a method to increase the level/activity of plasminogen, plasmin or miniplasmin can be applied or administered to prompt the oral health.

Compositions and Treatments

The active agents of the invention are used for modulating the biological activity of a drug target, and they are used in the treatment of conditions in which degradation of ECM, host defense and/or impairment of wound healing are observed. In particular, they may be used for preventing and treating periodontal disease, healing of periodontal wounds and prompting oral health.

Accordingly, the active agents of the invention may be formulated into pharmaceutical compositions for administration to subjects in a biologically compatible form suitable for administration in vivo. By biologically compatible form suitable for administration in vivo meant a form of the active agent to be administered in which any toxic effects are outweighed by the therapeutic effects. The active agent may be administered to living organisms including humans, and animals. An active amount of the active agent of the present invention is defined as an amount effective, at dosages and for periods of time necessary to achieve the desired result. For example, a therapeutically active amount of an active agent may vary according to factors such as the disease state, age, sex, and weight of the individual, and the ability of antibody to elicit a desired response in the individual. Dosage range may be adjusted to provide the optimum therapeutic response. For example, several divided doses may be administered daily or the dose may be proportionally reduced as indicated by the exigencies of the therapeutic situation.

The composition(s) may be administered in a convenient manner such as by injection (subcutaneous, intravenous, etc.), oral administration, inhalation, rectal, administration or transdermal application. Depending on the route of administration, the active agent(s) may be coated in a material to protect the agent from the action of enzymes, acids and other natural conditions that may inactivate the agent. Thus, suitable routes of administration include topical, intravenous, intramuscular, intradermal, oral, rectal, and intravaginal administration. A preferred administration route is topical administration or oral administration.

The compositions described herein can be prepared by methods known per se for the preparation of pharmaceutically acceptable compositions which can be administered to subjects, such that an effective quantity of one or more active agent(s) is combined in a mixture with a pharmaceutically acceptable vehicle. Suitable vehicles are described, for example, in Remington's Pharmaceutical Sciences (Mack Publishing Company, Easton, Pa., USA 1985). On this basis, the compositions include, albeit not exclusively, solutions of the active agents in association with one or more pharmaceutically acceptable vehicles or diluents, and contained in buffered solutions with a suitable pH and iso-osmotic with the physiological fluids.

Examples of vehicles that may be used in delivering the active agents according to the invention include, but are not limited to, gel, pastes, balms, waxes, lotions, skin creams, rinsing solutions, dried powers with/without bulking agent and various other formats for topical administration known in the art. The compositions may also be delivered locally in the form of a powder or solution sprayed, or gargling solutions. Alternatively, the compositions of the invention may be present in wound dressings, pads, band-aids, gauze, or other means applied to the area of interest, from which they are transferred to the needed area. Such devices also include slow-release devices, continually releasing plasminogen or other agents of the invention for a prolonged period of time, or can include instant-release devices, which releasing plasminogen or other agents of the invention immediately at the time for use.

After pharmaceutical compositions have been prepared, they can be placed in an appropriate container and labeled for treatment of an indicated condition. For administration of a composition of the invention, such labeling would include amount, frequency, and method of administration.

The compositions may be administered at regular intervals, e.g., once or twice a day, or added in dressings or slow-release devices which are changed as appropriate. In respect to prompt oral health, the composition may be administered instantly, by forming the composition at the time of use.

The above features and many other advantages of the invention will become better understood by reference to the following detailed description when taken in conjunction with the accompanying drawings.

FIG. 1. Photographs of normal healthy gum tissue (A), inflammatory gingivitis (B) and periodontal infection periodontitis (C).

Figure 2:
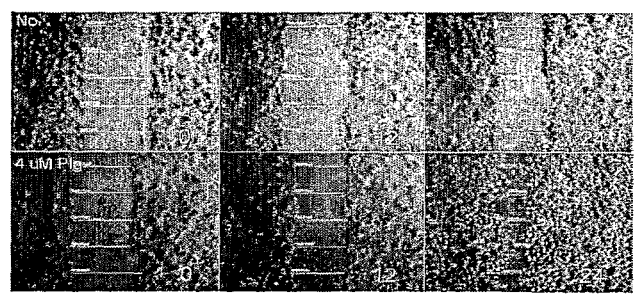
Figure 2:
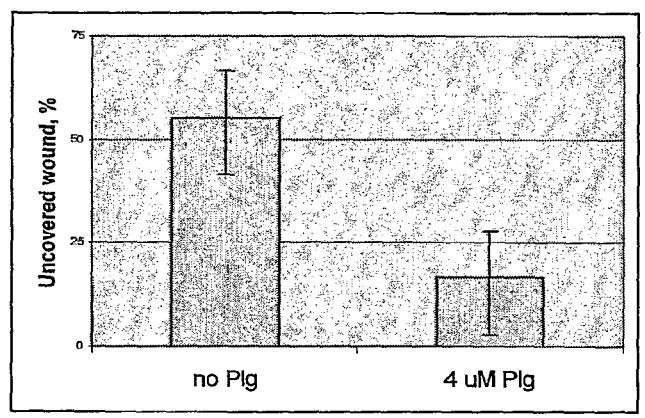

FIG. 2. Presence of plasminogen in growth medium promotes keratinocyte migration in an in vitro wound healing model.

Figure 3:
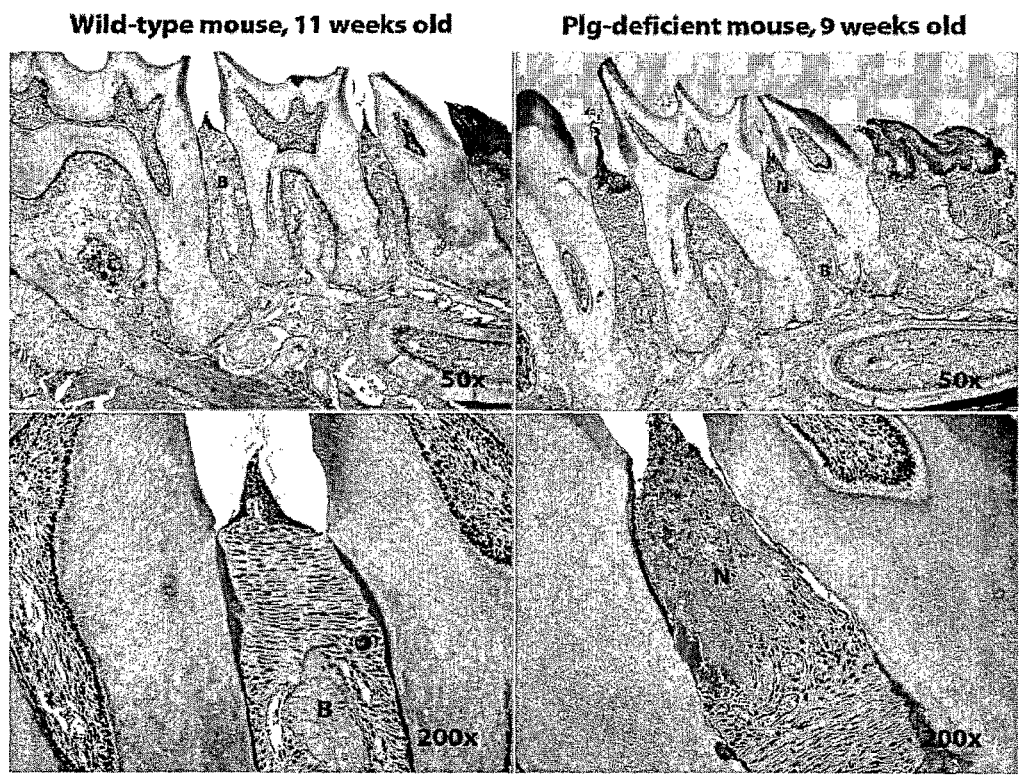

FIG. 3. Morphology of non-treated 8-12 week old wild type and plasminogen-deficient mice jaws. Note the necrotic tissue (N, in red) and severe degradation of bone septa (B) occur in the gum tissue of plasminogen-deficient mice, whereas the gum tissue in wild-type mice is completely normal. Under higher magnification (×200), the differences between wild-type and plasminogen-deficient mice are even more evident (lower panels). B, bone septa. N, necrotic tissue.

Figure 4:
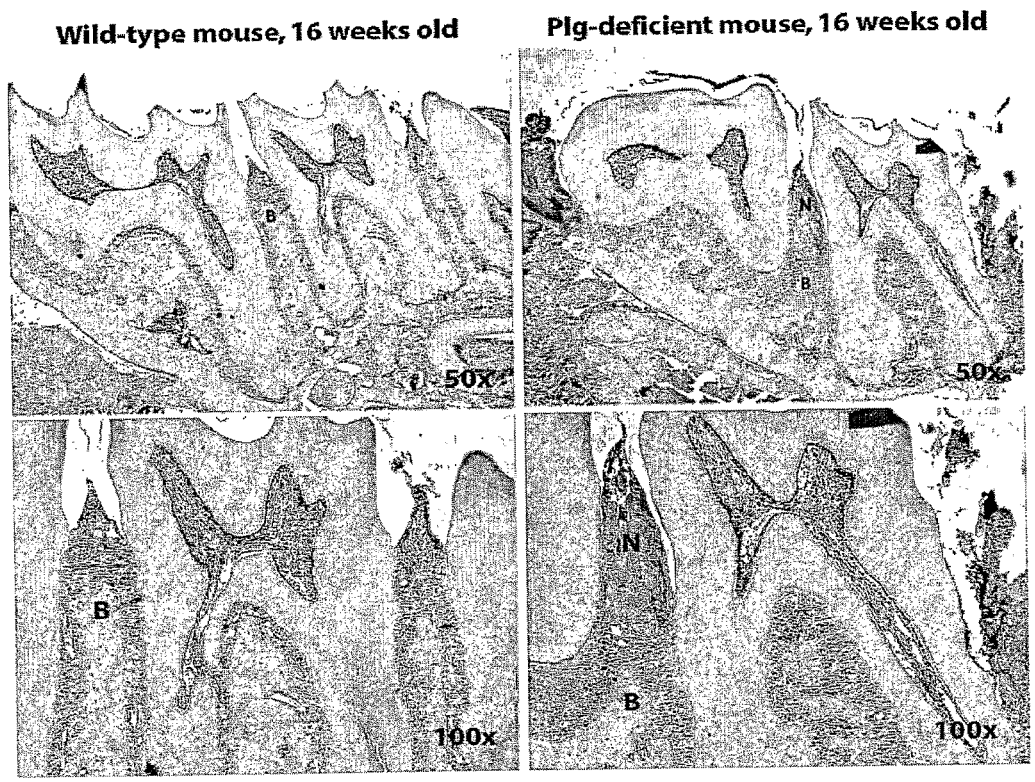

FIG. 4. Morphology of non-treated 12-16 week old wild type and plasminogen deficient mice jaws. Spontaneous periodontal disease in plasminogen-deficient mice at 12-16 weeks old is more severe than that of 8-12 weeks. Note the necrotic tissue (N, in red) and severe degradation of bone septa (B) occur in the gum tissue of plasminogen-deficient mice, whereas the gum tissue in wild-type mice is completely normal. Under higher magnification (×200), the differences between wild-type and plasminogen-deficient mice are even more evident (lower panels). B—bone septa, N—necrotic tissue.

Figure 5:
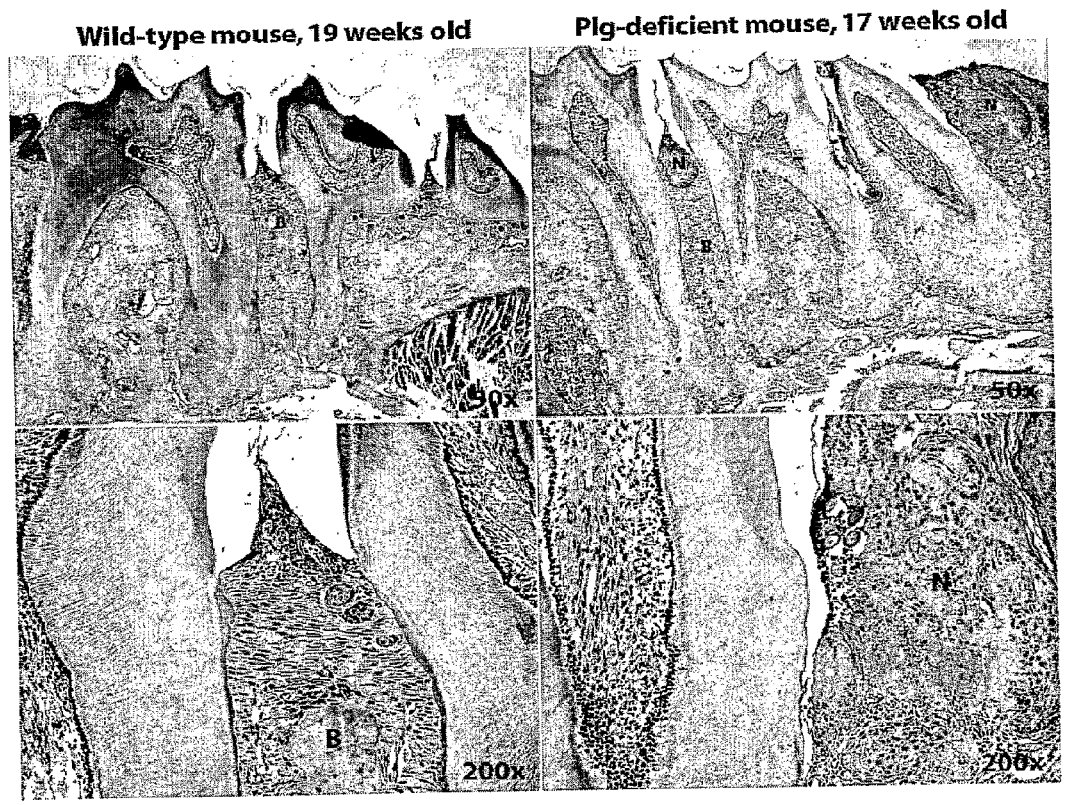

FIG. 5. Morphology of non treated 16-20 week old wild type and plasminogen deficient mice jaws. Spontaneous periodontal disease in plasminogen-deficient mice at 16-20 weeks old is more severe than that of 12-16 weeks. Note the necrotic tissue (N, in red) and severe degradation of bone septa (B) occur in the gum tissue of plasminogen-deficient mice (upper right panel), whereas the gum tissue in wild-type mice is completely normal (upper left panel). Under higher magnification (×200), the differences between wild-type and plasminogen-deficient mice are even more evident (lower panels). B—bone septa, N—necrotic tissue.

Figure 6:
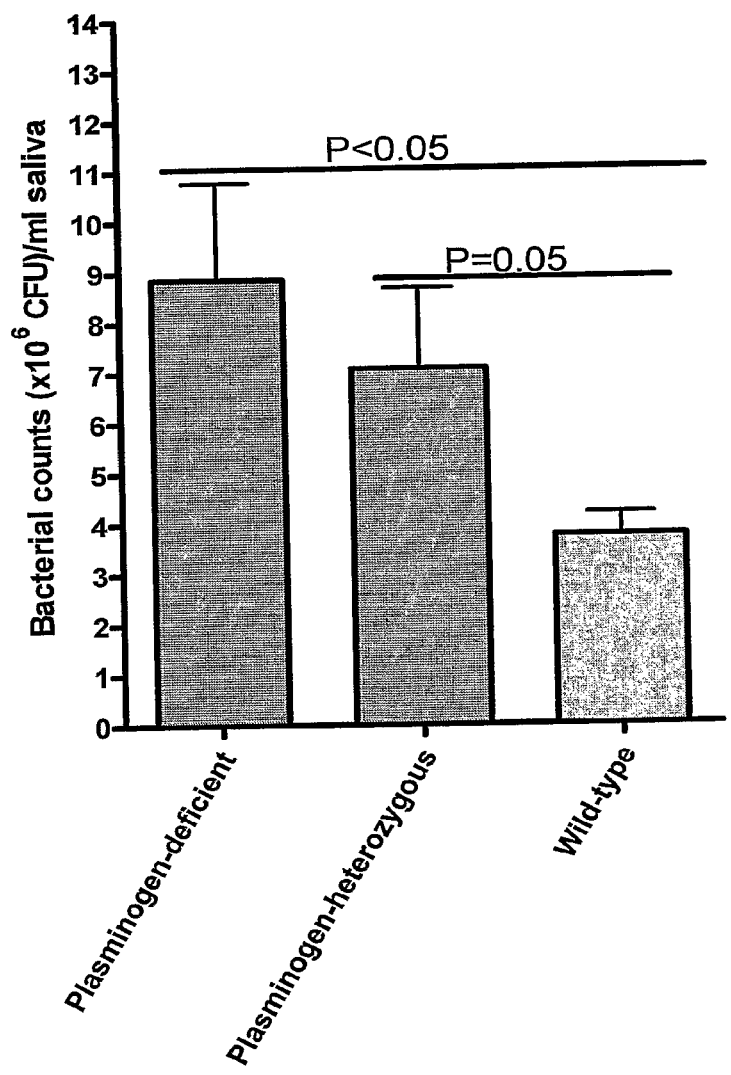

FIG. 6. Bacterial recovery from saliva of wild-type, plasminogen-heterozygous and plasminogen-deficient mice. Plasminogen-deficient and plasminogen-heterozygous mice have significantly higher numbers of bacteria in the saliva as compared to that of wild-type mice.

Figure 7:
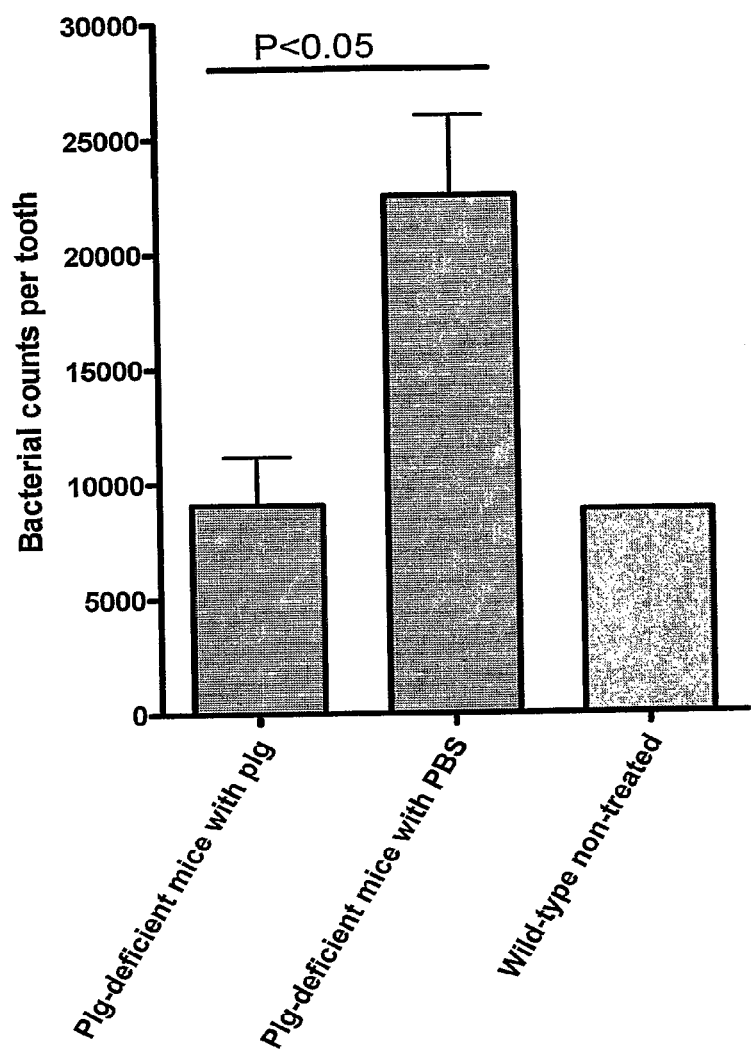

FIG. 7. Bacterial recovery from the pulled-out teeth of plasminogen-deficient mice supplemented with human plasminogen, plasminogen-deficient mice supplemented with PBS and wild-type mice without any treatments.

Figure 8:
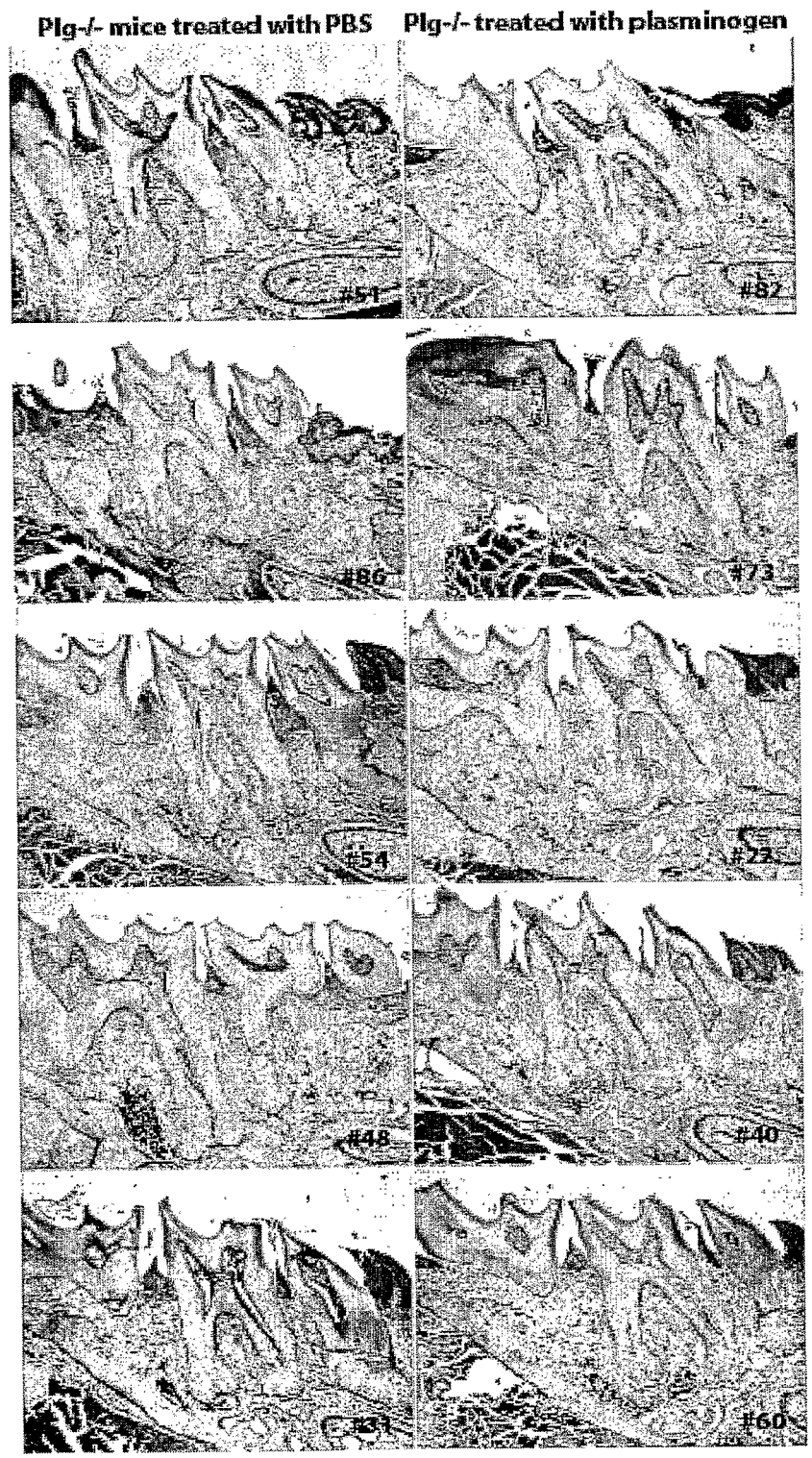

FIG. 8. Morphology of plasminogen-deficient mice supplemented with PBS or human plasminogen. Note in the PBS treated plasminogen-deficient mice, necrotic tissue was present in the gum tissue, surrounding collagen tissue started to detach from teeth and bone resorption had taken place (left panels). However, supplementation of human plasminogen in plasminogen-deficient mice had completely recovered the cellular and tissue structure in the periodontal tissue. Magnification, ×50.

Figure 9:
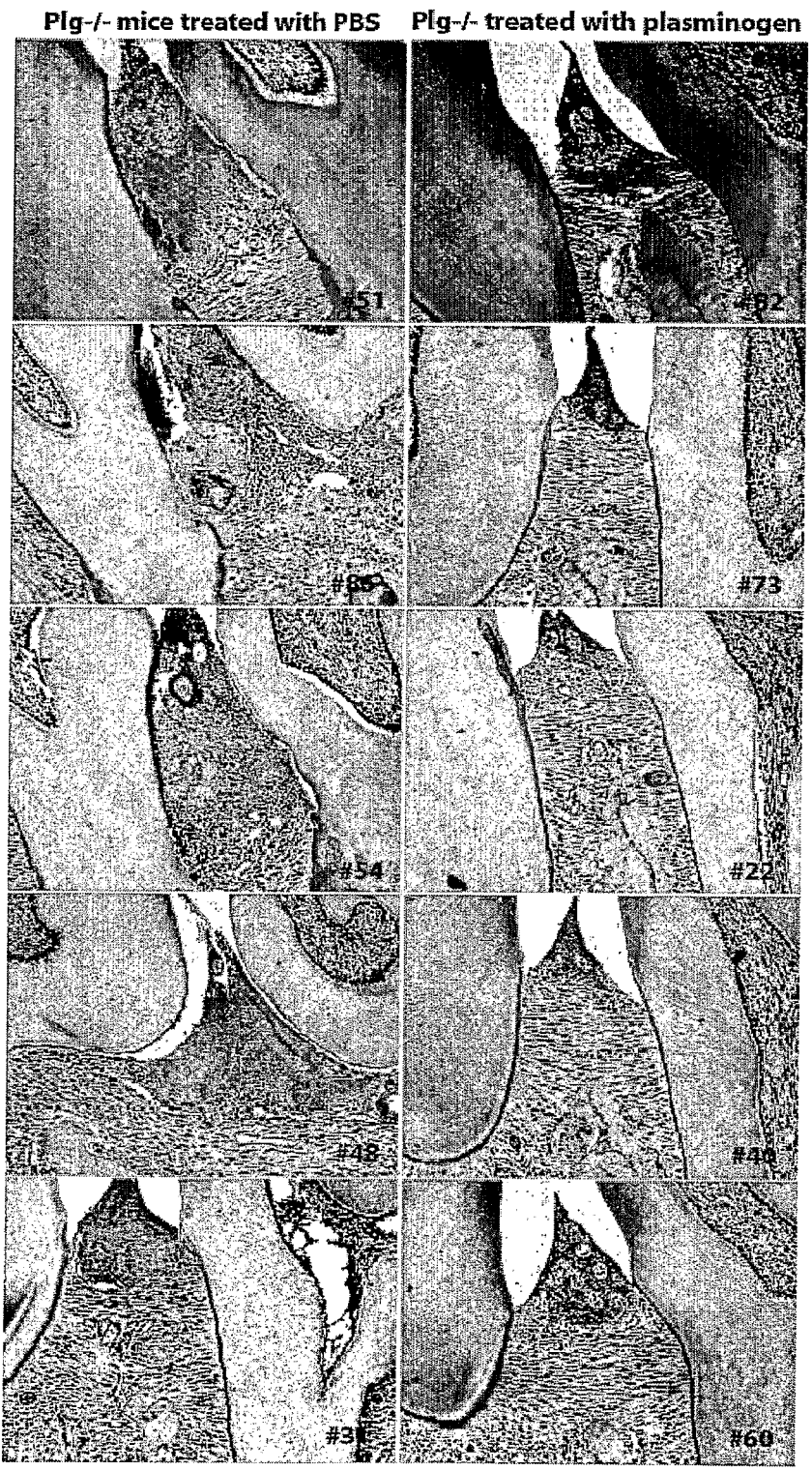

FIG. 9. Morphology of plasminogen-deficient mice supplemented with PBS or human plasminogen under higher magnification (×50).

Figure 10:
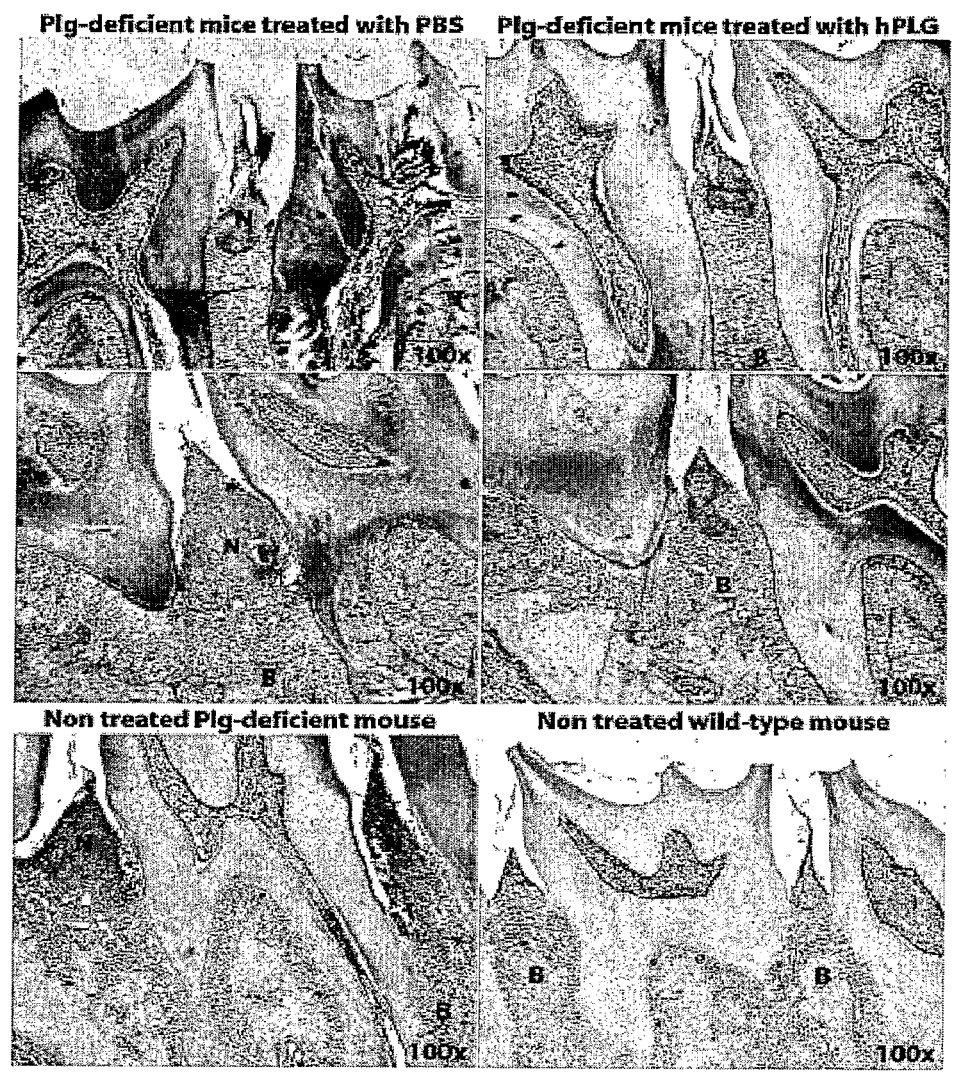

FIG. 10. Morphology of plasminogen-deficient mice supplemented with PBS or human plasminogen by oral injections. Note in the PBS treated plasminogen-deficient mice, necrotic tissue is present in the gum tissue, surrounding collagen tissue started to detach from teeth and bone resorption had taken place (upper two left panels). However, supplementation of human plasminogen in plasminogen-deficient mice had recovered the cellular and tissue structure in the periodontal tissue. Magnification, 100×.

Figure 11:
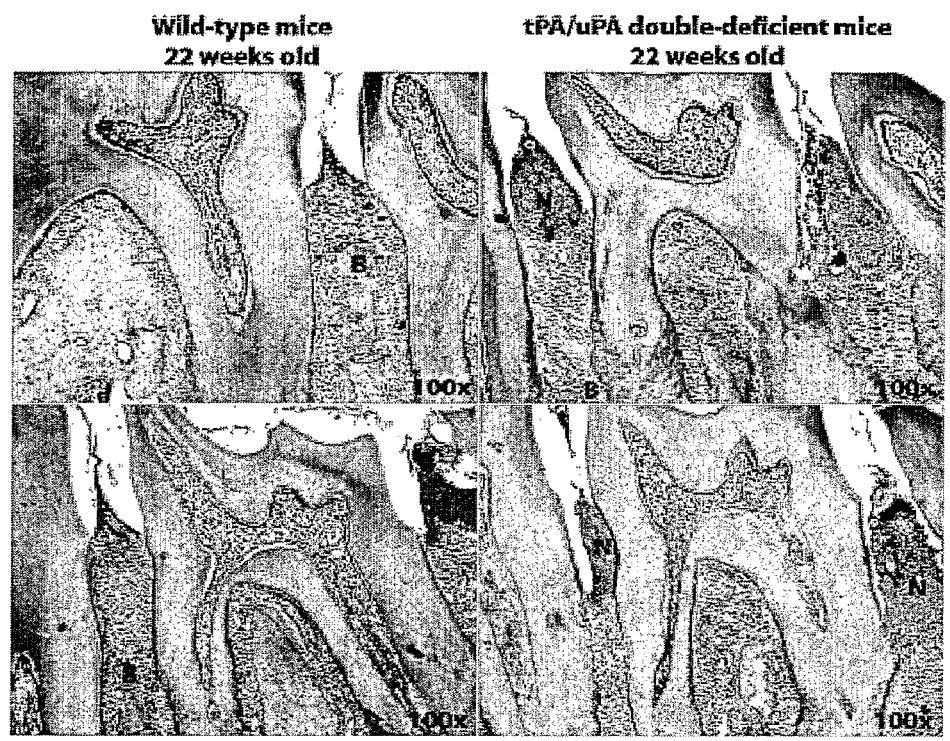

FIG. 11. Morphology of non-treated 22 week old wild type (left panels) and tPA/uPA double-deficient (right panels) mice jaws. Note the necrotic tissue (N, in red) and severe degradation of bone septa (B) occurs in the gum tissue of tPA/uPA double-deficient mice, where the gum tissue in wild-type mice is completely normal. B, bone septa. N, necrotic tissue.

Figure 12:
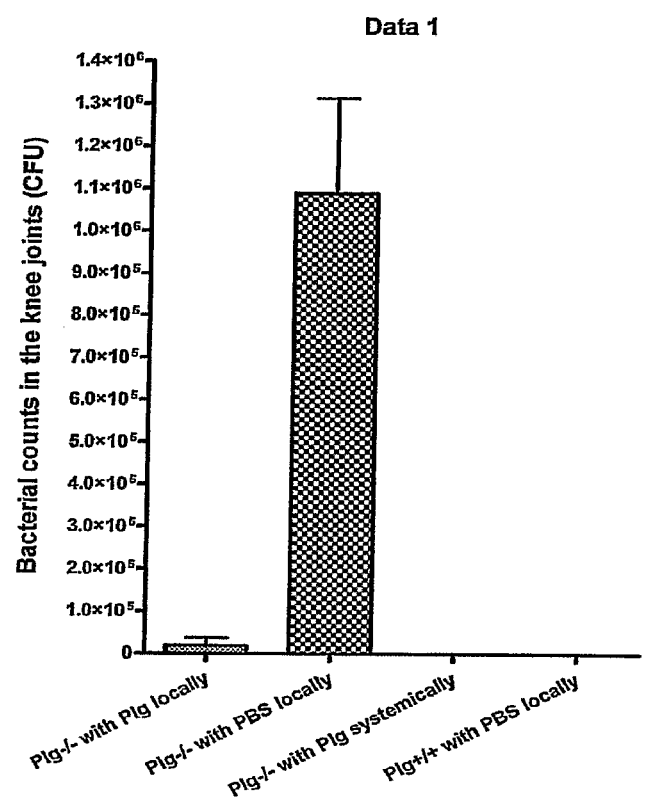

FIG. 12. Bacterial numbers in knee joints of plg−/− and plg+/+ mice with different local and systemic treatments after inoculation of 1×10$^6$ CFU of S. aureus Phillips at the knee joints.

Figure 13:
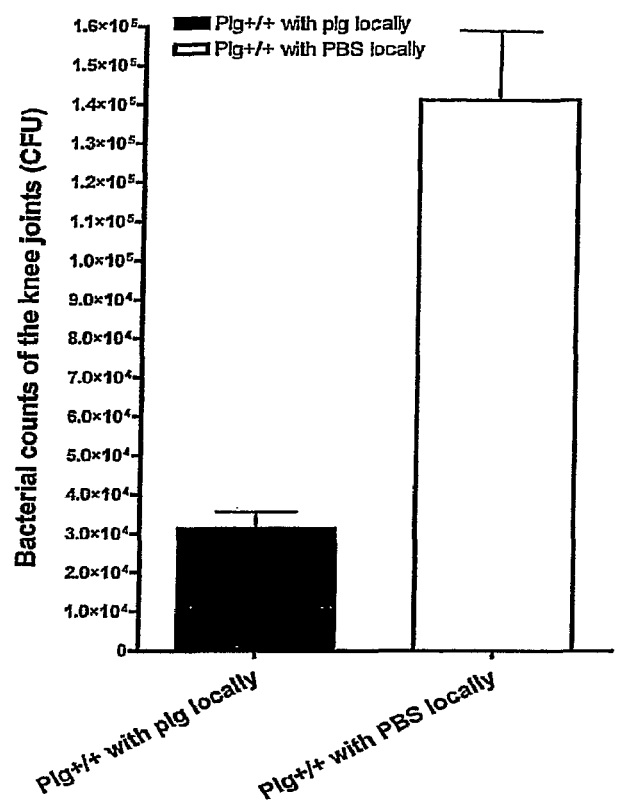

FIG. 13. Bacterial numbers in knee joints of plg+/+ mice after local injection with Plg (closed box) or PBS (open box) 3 days after inoculation of S.aureus at the knee joints. Note in wild-type mice locally injected with Plg the bacterial number is significantly lowered for 5 folds than that of wild-type locally injected with PBS.

DEFINITIONS

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

"A compound of the group comprising: plasminogen, plasmin, a component of the plasminogen activation pathway, a plasminogen analogue, such as mini-plasmin, a plasmin analogue, an analogue of a component of the plasminogen activation pathway, a plasminogen activator" refers to a compound that directly or indirectly provides the effect of plasminogen or plasmin, respectively.

"A component of the plasminogen activation pathway" refers to plasminogen, Lys-plasminogen, Glu-plasminogen, variants and analogues of plasminogen comprising one ore more domains of plasminogen such as one ore more of the kringle domains and the proteolytic domain exemplified by mini-plasminogen; plasmin and variants and analogues of plasmin comprising at least one ore more domains of plasmin such as one or more of the kringle domains and the proteolytic domain, exemplified by mini-plasmin and delta-plasmin; a plasminogen activator having the final effect of activating plasminogen, e.g. by a cascade of events resulting in the formation or activation of plasminogen exemplified by uPA and tPA and variants and analogues of tPA and uPA comprising one or more domains of tPA or uPA such as one ore more of the kringle domains and the proteolytic domain. Variants of plasminogen, plasmin, tPA and uPA include all naturally occurring genetic variants of human as well as other mammalian forms of these proteins, as wells as mutant variants of these proteins obtained by conservative amino acid replacements. An "analogue" of plasminogen or plasmin is a compound providing essentially an analogous effect as plasminogen or plasmin, respectively, as measured by enzymography, ELISA (enzyme-linked immunosorbent assay) and FACS (fluorescence activated cell sorter), There is also an assay for measuring levels of converted plasmin activity as described previously: Ny, A., Leonardsson, G., Hagglund, A. C., Hagglof, P., Ploplis, V. A., Carmeliet, P., and Ny, T. (1999). Ovulation in plasminogen-deficient mice. Endocrinology 140, 5030-5035.). An "analogue" of a component of the plasminogen activation pathway is a compound providing essentially an analogous effect as a component of the plasminogen activation pathway as measured by the levels of plasmin activity that this analogue activates.

"Periodontal disease" is a common inflammatory disorder caused by the interplay between the specific subgingival microorganisms and the host immune and inflammatory response. Periodontal diseases range from simple gum inflammation to serious disease that result in major damage to the soft tissue and bone that support the teeth. In the worst cases, teeth are lost. The bacteria cause inflammation of the gums that is called "gingivitis." In gingivitis, the gums become red, swollen and can bleed easily. Gingivitis is a mild form of gum disease that can usually be reversed with daily brushing and flossing, and regular cleaning by a dentist or dental hygienist. This form of gum disease does not include any loss of bone and tissue that hold teeth in place. When gingivitis is not treated, it can advance to "periodontitis" (which means "inflammation around the tooth.") In periodontitis, gums pull away from the teeth and form "pockets" that are infected. The body's immune system fights the bacteria as the plaque spreads and grows below the gum line. Bacterial toxins and the body's enzymes fighting the infection actually start to break down the bone and connective tissue that hold teeth in place. If not treated, the bones, gums, and connective tissue that support the teeth are destroyed. The teeth may eventually become loose and have to be removed. Another type of periodontal disease, peri-implantitis, occurs as a biological complication after surgical implantation of an alloplastic material into the jawbone. Periimplantitis is an inflammatory/infectious process affecting the tissues around an osseointegrated implant in function, resulting in loss of supporting bone. Periimplantitis may lead to complete disintegration and implant loss even if extensive treatment aiming at resolving the periimplant infection has been performed. Periimplantitis also happens as reversible inflammatory/infectious changes of the peri-implant soft tissues without any bone loss, sometimes referred to as peri-implant mucositis. In the current patent, the definition of periodontal disease includes at least periodontitis, gingivitis, periimplantitis and peri-implant mucositis.

"Infectious periodontal disease" is periodontal disease caused by infection, in contrast to e.g. ligneous periodontitis. E.g. infectious periodontitis can be caused by bacterial, viral or fungal infection.

"Bacterial periodontal disease" is caused by bacterial infection.

"Periodontal wound" refers to the traumatic wounds and surgical wounds occurring at the periodontal tissue of the mouth, including wounds at the tissues surrounding implants in the periodontal area.

"Oral health" refers to the standard of health of the oral and related tissues which enables an individual to eat, speak and socialize without active disease, discomfort or embarrassment and which contributes to general well-being. Major indications of oral health include the bacterial flora in the saliva and gum tissue, as well as the tissue necrosis and inflammation in the gum tissue. Oral health is integral to general health and should not be considered in isolation.

"Derivatives of plasmin/plasminogen" refers to e.g. kringle domains of plasmin or plasminogen, protein fragments of plasmin or plasminogen, mini-plasminogen and mini-plasmin as well as the synthetic derivatives of plasmin or plasminogen "Mini-plasminogen" refers to the C-terminal fragment of native plasminogen, which includes the enzyme active site. The Mr of miniplasminogen is 38000. Activation with urokinase or streptokinase yields a two-chain enzyme with substrate specificity extremely similar to that of plasminogen, which is termed as 'mini-plasmin'.

"Necrosis" refers death of tissue in the body. This happens when not enough blood is supplied to the tissue, whether from injury, radiation, or chemicals. Necrosis is not reversible. There are many causes of necrosis including injury, infection, cancer, infarction, invenomation, chronic wounds, ulcers and inflammation.

"Topical" and "topical application" refer to non-systemic, local, administration of an active ingredient. Thus, topical application can refer to application of an active ingredient to the external surface of a wound.

The "activity" of a protein or compound refers to the effect the protein or compound has on a specific reaction, and is a measure of its ability to affect, modulate, participate in, or promote the reaction. Generally, the activity of a protein or other compound can be measured. For example, in the case of enzymes such as plasmin, PA, and MMPs, and modulators enzyme activity can be expressed as the rate at which the product of the reaction is produced, represented, e.g., as the amount of product produced per unit of time and of enzyme (e.g., concentration or weight). In the case of modulators such as PAs, activity can refer to the ability of the modulator to inhibit or promote, increase or decrease, up- or down-regulate, the rate of a reaction or the amount of product formed from the reaction.

A "wound" is a break in the structure of an organ or tissue, including epithelium, connective tissue, and muscle tissue, caused by an external agent. Examples of wounds include, but are not limited to, bruises, grazes, tears, cuts, punctures, and burns. Other particular types of wounds are those that are a consequence of plastic surgery procedures.

"Treatment" of a subject, or "treating" a subject for a disease or condition herein means reducing or alleviating clinical symptoms of the disease or condition such as impaired or slow wound-healing.

"Enhancing" wound healing means increasing the speed by which the wound heals. Alternatively, "enhancing" wound healing means reducing the formations of scar tissue during or after healing.

A "subject" herein includes both human and non-human animals. Non-human animals include, without limitation, laboratory animals such as mice, rats, rabbits, hamsters, guinea pigs, etc.; domestic animals such as dogs and cats; and farm animals such as sheep, goats, pigs, horses, and cows. A non-human animal of the present invention may be a mammalian or non-mammalian animal; a vertebrate or an invertebrate.

A "control", "control value" or "reference value" in an assay is a value used to detect an alteration in, e.g., the treatment of periodontal disease, healing of periodontal wounds and prompting oral health, or any other assays described herein.

A subject "at risk for", "predisposed to", or "susceptible to" a disease or condition means that the risk for the individual to contract or develop the disease or condition is higher than in the average population.

A "deficiency" of a compound means that the amount, level, or concentration of the compound is significantly lower than a control value. For example, in a plasminogen-deficient animal, the body fluid and tissue levels of plasminogen are significantly lower than in a wild-type animal.

As used herein, "about" or "approximately" shall mean within 50 percent, preferably within 20 percent, more preferably within 5 percent, of a given value or range.

A value which is "substantially different" from another value can mean that there is a statistically significant difference between the two values. Any suitable statistical method known in the art can be used to evaluate whether differences are significant or not. A "statistically significant" difference means a significance is determined at a confidence interval of at least 90%, more preferably at a 95% confidence interval.

Abbreviations

Abbreviations used in the present disclosure include the following:
uPA=Urokinase-type plasminogen activator;
PA=Plasminogen activator;
MMP=Matrix metalloproteinase;
TIMP=Tissue inhibitor of metalloproteinase;
tPA=Tissue-type plasminogen activator;
Plg=Plasminogen
ECM=Extracellular matrix

EXAMPLES

The invention is further described by means of the following examples. However, these examples are only illustrative of the invention, and in no way limits the scope and meaning of the invention. Indeed, many modifications and variations of the invention will be apparent to those skilled in the art upon reading this specification, and can be made without departing from its spirit and scope.

Example 1

In Vitro Keratinocyte Migration is Dependent on the Relative Amounts of Plasminogen Since wound healing involves a huge number of different factors, cells and processes, a simplified in vitro model is included to delineate the possible plasminogen effect on cell migration.

Methods:

DOK (early neoplastic/dysplastic human oral keratinocytes) cells were incubated in cell culture media After starving, DOK cells were incubated in DMEM cell culture medium, containing hydrocortisone, glutamine, penicillin/streptomycin, 10% plasminogen depleted fetal bovine serum, and in the absence or presence of human plasminogen. At 0 h, a standard scratch was made on the keratinocyte layer in order to induce in vitro wound healing model. At different time points (0 h, 12 h and 24 h) the keratinocyte migration was documented under ZEISS microscope.

Results:

DOK (early neoplastic/dysplastic human oral keratinocytes) cell migration seems to be almost arrested in the absence of plasminogen in the culture media during the experimental period (FIG. 2A, upper panels). However, in the presence of plasminogen in the culture media, keratinocyte migration appears to be enhanced as compared to that in the plasminogen-depleted media (FIG. 2A, lower panels). After 24 hours of plasminogen exposure (4 µM), the edges of such in vitro wounds are close to be fused (FIG. 2B). Furthermore, cell migration rate appears to be plasminogen concentration dependent. This experiment clearly indicates that plasminogen is important for faster wound closure and enhanced healing rate of damaged tissue in vitro.

Example 2

Spontaneous Development of Periodontal Disease in Plasminogen-deficient Mice

Methods:

This experiment is dedicated to investigate the importance of plasminogen in the development of periodontal disease by analyzing wild-type and plasminogen-deficient mice at different age.

Plasminogen-deficient (plg deficient) and wild-type (wt) mice were divided into three age groups (5-8 mice per genotype per group): Group I: 8-12 weeks old; Group II: 12-16 weeks old; Group III: 16-20 weeks old. The development of periodontal disease was followed by analyzing the tissue samples of each genotype and age group.

To analyze the tissue samples, the lower and upper jaws are separated from the cranium, de-fleshed from gross soft tissue such as tongue, and fixed in 4% paraformaldehyde (PFA) for 24 hours. Thereafter, samples were transferred to the decalcification solution to remove calcium from the bone tissue. After four weeks of decalcification process specimens were embedded in paraffin and sectioned at 5 µm thickness for morphological staining. Safranin O staining was used for morphological analysis, thus cartilage and mucin are stained in dark red, bone structures and teeth are blue, and the cell nuclei are stained dark blue.

Results:

Morphological analysis of gum tissue surrounding the teeth at 8-12 week old shows that wild type mice have no inflammation or detachment of collagen tissue from the tooth surface. In contrast, all the plg deficient mice show distinct signs of initial gingivitis stages—inflammation, collagen tissue detachment from the teeth, necrotic tissue formation between the teeth and degradation of bone septa and underlying jaw bone (FIG. 3). Whereas wild-type mice have healthy oral cavity up to 20 weeks age (FIGS. 3, 4, 5), in the plasminogen-deficient mice, gingivitis progresses with age to periodontitis: gum tissue is severely inflamed, necrotic tissue forms deep in the soft tissue and evident bone septa destruction (FIGS. 4, 5). These data clearly demonstrate that plasminogen-deficient mice spontaneously develop severe periodontal disease and the disease severity progresses with age.

Example 3

Plasminogen-deficient Mice Have Significantly Higher Amounts of Bacteria in the Saliva than that of Wild-type Mice Methods:

Wild-type, plasminogen-heterozygous and plasminogen-deficient mice at age between 16-20 weeks old were used in this study (Table 1). Salivary sampling of mice was performed by collecting the saliva from the mouth with a sterile pipette tip and transferred into anaerobic medium for immediate culturing.

Results:

5 ul of salivary samples were successfully collected from wild-type and plasminogen-heterozygous mice. However, due to the general dry conditions of the mouths in plasminogen-deficient mice, the amount of possible of salivary samples resulted in variations, ranging from 1.0 ul to 5.0 ul. Bacterial recovery showed that plasminogen-deficient mice have nearly $9.0 \times 10^6$/ml of bacteria in saliva, the highest in the three groups and significantly higher than that of wild-type mice. Importantly, plasminogen-heterozygous mice also have significantly higher amounts of bacteria than that of wild-type mice (FIG. 6). These data clearly indicate that plasminogen plays a critical role in maintaining the resistance against oral bacteria. Furthermore, the number of bacteria seems to be critically dependent on the relative amounts of plasminogen, which suggest a therapeutic importance for plasminogen as a novel drug to prompt oral health.

Example 4

Supplementation of Human Plasminogen in Plasminogen-deficient Mice Successfully Improves the Clinical Conditions of Spontaneous Periodontal Disease in These Mice Methods:

Ten plasminogen-deficient (8-12 week old) mice were randomly divided into plasminogen and PBS treatment groups (5 mice per group). From day 0 to day 9 mice were injected intravenously daily with 100 µl of human plasminogen (10 mg/ml) or PBS. At day 10 mice were sacrificed. For the left side jaws, molar teeth were pulled out for the recovery of bacteria. Right side jaws were processed for decalcification, paraffin embedding and morphological staining. Three non treated wild type mice of the same age were included as controls in the experiment.

Results:

Bacterial recovery from the pulled-out tooth samples showed that plasminogen-deficient mice supplemented with human plasminogen have significantly lowered numbers of bacteria as compared to that with PBS supplementation (FIG. 7). These data indicate that plasminogen is essential in host defense against bacterial colonization on the teeth.

As expected, severe periodontal disease occurred in all the 5 PBS treated plasminogen-deficient mice: necrotic tissue was present in the gum tissue, surrounding collagen tissue started to detach from teeth and bone resorption had taken place (FIG. 8 and FIG. 9, left panels). Plasminogen-deficient mice supplemented with human plasminogen had com- pletely recovered the cellular and tissue structure: no inflammation was observed in the gum tissue, necrotic tissue had been removed and collagen tissue remodeling had taken place (FIG. 8 and FIG. 9, right panels). For the 3 non-treated wild-type mice, the morphological analysis showed similar normal tissue structure as in FIG. 3. This data clearly show that plasminogen plays a pivotal role in maintaining normal tissue structure and function against periodontal disease.

Example 5

Local Supplementation of Human Plasminogen at the Gum Tissue in Plasminogen-deficient Mice Successfully Improves the Clinical Conditions of Spontaneous Periodontal Disease in These Mice Methods:

Ten plasminogen-deficient (16-20 week old) mice were randomly divided into plasminogen and PBS treatment groups (5 mice per group). From day 0 to day 9 10 µl of human plasminogen (10 mg/ml) was locally injected daily to the gum tissue of both sides of the lower jaws of plasminogen-deficient mice. For control PBS-treated group, 10 µl of PBS was locally injected daily to the gum tissue of both sides of the lower jaws of plasminogen-deficient mice. At day 10 mice were sacrificed and performed for morphological studies. Three non-treated wild-type mice and three non-treated plasminogen-deficient mice were used as non-treatment controls.

To analyze the tissue samples, the lower and upper jaws are separated from the cranium, de-fleshed from gross soft tissue such as tongue, and fixed in 4% PFA for 24 hours. Thereafter, samples were transferred to the decalcification solution to remove calcium from the bone tissue. After four weeks of decalcification process specimens were embedded in paraffin and sectioned at 5 µm thickness for morphological staining. Safranin O staining was used for morphological analysis, thus cartilage and mucin are stained in dark red, bone structures and teeth are blue, and the cell nuclei are stained dark blue.

Results:

Local injection of plasminogen at the gum tissue successfully diminished the severity of periodontal disease in plasminogen-deficient mice. As expected, severe periodontal disease occurred in all the 5 PBS treated plasminogen-deficient mice: necrotic tissue was present in the gum tissue (N), surrounding collagen tissue started to detach from teeth and bone resorption had taken place (FIG. 10, two upper panels to the left). Plasminogen-deficient mice locally supplemented with human plasminogen had recovered the normal cellular and tissue structure to a large extent: low levels of inflammation were observed in the gum tissue, necrotic tissue had been removed and collagen tissue remodeling had taken place (FIG. 10, two upper panels to the right). For the 3 non-treated wild-type and plasminogen-deficient mice, the morphological analysis showed similar tissue structure as in FIG. 3, respectively. This data clearly show that local supplementation of plasminogen provides an effective and potent way to treat periodontal disease.

Example 6

Spontaneous Development of Periodontal Disease in uPA and tPA Double-deficient Mice Methods:

This experiment is dedicated to investigate the importance of plasmin in the development of periodontal disease by analyzing the periodontal tissue in wild-type and tPA/uPA double-deficient mice. tPA and uPA double-deficient mice were created in our lab in order to create mice lacking of plasminogen activation. These mice, although containing plasminogen in their bodies, can not convert the plasmin precursor to active plasmin. Therefore, data from these mice can directly address of the importance of active plasmin in the host defense against spontaneous periodontal disease.

The occurrence of periodontal disease in tPA/uPA double-deficient mice and their wild-type littermates at the age of 22 weeks old was followed by analyzing the tissue samples of each genotype.

To analyze the tissue samples, the lower and upper jaws are separated from the cranium, de-fleshed from gross soft tissue such as tongue, and fixed in 4% paraformaldehyde (PFA) for 24 hours. Thereafter, samples were transferred to the decalcification solution to remove calcium from the bone tissue. After four weeks of decalcification process specimens were embedded in paraffin and sectioned at 5 μm thickness for morphological staining. Safranin O staining was used for morphological analysis, thus cartilage and mucin are stained in dark red, bone structures and teeth are blue, and the cell nuclei are stained dark blue.

Results:

Morphological analysis of 22 weeks old wild-type and tPA and uPA double-deficient mice shows that whereas wild type mice have no inflammation or detachment of collagen tissue from the tooth (FIG. 11, left panels), all the four tPA and uPA double-deficient mice show severe periodontal disease: gum tissue is severely inflamed, necrotic tissue (N) is formed deep in the soft tissue and evident bone septa destruction (B) had taken place (FIG. 11). These data clearly demonstrate that tPA and uPA double-deficient mice spontaneously develop severe periodontal disease, indicating that active plasmin is also critical in the maintenance of normal periodontal health.

In the following examples, we are going to describe the findings we have in the studies of bacterial arthritis and a study we are going to perform. We believe we will get similar promising data as we had in the bacterial arthritis study. Although the data we have are from the study of bacterial arthritis, we consider these results strongly shed light to the promising outcoming when similar studies are performed on periodontal area. And therefore these results suggest that local injection of human plasminogen in the periodontal area can also restore the normal host defense against periodontal disease in plg−/− mice. This conclusion is based on the consideration of following reasons:

1. The host defense mechanisms are in large extent similar in the knee joint areas and in the periodontal areas, in that in both situations inflammatory cells are activated and migrated to the infectious area, bacteria are killed by the activated inflammatory cells and other molecules, expression of cytokine network are enhanced, necrotic tissue are removed and tissue remodeling occurred throughout the host defense process.
2. S. aureus is a clinical pathogen that plays important roles in the infectious processes during both periodontitis and bacterial arthritis. Therefore, the data obtained from the studies of S. aureus-induced bacterial arthritis most likely represent a general phenomenon in spite of the specific tissue location of the infection.
3. The local injection method that was used in the bacterial arthritis model has also been used in the periodontitis study (see Example 5) and has shown positive results where local injection of plasminogen reduced spontaneous periodontitis in plg−/− mice. These similarities further indicate that the results obtained from bacterial arthritis represent a general mechanism that also underlies the periodontal disease.

Therefore, we would like to use data from our studies on bacterial arthritis (Examples 7 and 8) to support our claims in the current patent application. The importance of the data from bacterial arthritis study is that: first, the results from Example 7 indicate that local injection of plasminogen restores the host defense capacity (e.g. killing bacteria) in a induced infection model in plg−/− mice; In addition, the results from Example 8 indicate that local injection of plasminogen in a induced infection model further enhances the normal host defense capacity (e.g. killing bacteria) in normal wild-type mice. Furthermore, based on these reasons, we also include in the current patent application another example that we going to perform (Example 9). In this example, we describes a clinical model of induced periodontal disease and we believe that application of plasminogen can restore the host defense in plg−/− mice and further enhance the normal host defense in wild-type mice or other species.

Example 7

Local Supplementation of plg$^{-/-}$ Mice with Human Plasminogen (hPlg) Restored the Normal Host Defense Against Bacterial Infection in the Knee Joints Methods Bacterial arthritis was induced by local inoculation of 1×10$^6$ CFU of S. aureus Phillips in 10 μl sterile PBS into both knee joints of mice. 15 minutes after bacterial inoculation, one side of the knee joints of 6 plg$^{-/-}$ mice was supplemented with 40 μl of human plasminogen (10 μg/μl in PBS, Biopool, Umcǎ, Sweden) by local injections around the knee joint tissue. Thereafter human plasminogen was supplemented at 24-hour intervals for 7 days. As controls for local injections, 6 plg$^{-/-}$ mice were locally injected around the knee joint tissue with 40 ul of sterile PBS alone at 15 minutes after bacterial inoculation, and thereafter at 24-hour intervals during 7 days experimental period. As controls for wild-type mice, 2 plg+/+ mice were given 40 ul of sterile PBS alone at 15 minutes after bacterial inoculation, and thereafter every 24 hours for 7 days. As controls for plg−/− mice with systemic injections, 2 plg−/− mice were given 100 μl human plasminogen (10 μg/μl) intravenously 1 hour before bacterial inoculation and thereafter every 24 hours for 7 days.

Mice were sacrificed at day 7 after bacterial inoculation and the knee joints were taken and homogenized in 1 ml sterile PBS. After serial dilutions, the solutions of homogenates were spreaded on LB agar plates and incubated at 37° C. overnight. Viable bacterial colonies were then counted to evaluate the number of S. aureus bacteria in each homogenate.

Results 7 days of local injection of plasminogen to plg−/− mice inoculated with S. aureus successfully and significantly decreased the amounts of bacteria to 100-folds as compared to the PBS local treatment in these mice. Both plg−/− mice with systemic injection of human plasminogen or plg+/+ mice with local injection of PBS have also successfully killed *S. aureus* in their knee joints. These data (Table 1) clearly demonstrate that local injection of human plasminogen can restore the normal bacterial killing capacity in the plg−/− mice.

TABLE 1

Bacterial number in plg−/− and plg+/+ mice with different local and systemic treatments at day 3 after inoculation of 1 ×10⁶ CFU of *S. aureus* Phillips

| Groups | Number of samples | Mean number of bacteria (Mean ± SD, × 10⁶ CFU) |
|---|---|---|
| Plg−/− with local injection of hPlg | 6 | 0.019 ± 0.044* |
| Plg−/− with local injection of PBS | 6 | 1.09 ± 0.55 |
| Plg−/− with systemic injection of hPlg | 2 | 0.00075 ± 0.0011* |
| Plg+/+ with local injection of PBS | 2 | 0.00065 ± 0.00092* |

*$P < 0.05$, compared to the group of plg−/− mice with local injection of PBS.

Example 8

Local Supplementation of plg$^{+/+}$ Mice with Human Plasminogen Enhances the Host Defense Against Bacterial Infection in the Knee Joints Methods Bacterial arthritis was induced by local inoculation of 1×10⁶ CFU of *S. aureus* Phillips in 10 μl sterile PBS into knee joints of mice. 15 minutes after bacterial inoculation, one side of the knee joints of 7 plg$^{+/+}$ mice was supplemented with 50 μl of human plasminogen (hPlg, 10 μg/μl in PBS, Biopool, Umcå, Sweden) by local injections under the knee skin and around the knee joint tissue. Thereafter human plasminogen was supplemented in the same pattern at 24-hour intervals from day 0 to day 2. As controls for local injections, 7 plg$^{+/+}$ mice were locally injected under the knee skin and around the knee joint tissue with 50 ul of sterile PBS alone at 15 minutes after bacterial inoculation, and thereafter the same local injections were performed at 24-hour intervals from day 0 to day 2 of the experimental period.

Mice were sacrificed at day 3 after bacterial inoculation and the knee joints were taken and homogenized in 1 ml sterile PBS. After serial dilutions, the solutions of homogenates were spreaded on LB agar plates and incubated at 37° C. overnight. Viable bacterial colonies were then counted to evaluate the number of *S. aureus* bacteria in each homogenate.

Results

Local injection at the knee joints of human plasminogen for 3 days in plg+/+ mice successfully and significantly reduced the living *S. aureus* number for 5 folds as the the control plg+/+ group treated PBS. These data clearly demonstrate that human plasminogen is a potent pro-inflammatory factor that potentiate the host defense against bacterial infection even in wild-type animal. These data (Table 2) further indicate that plasminogen is a novel anti-infectious drug candidate for clinical use.

TABLE 2

Bacterial number in wild-type (plg+/+) mice locally injected with human plasminogen or PBS at day 3 after inoculation of 1 ×10⁶ CFU of *S. aureus* Phillips. Note in wild-type mice locally injected with Plg the bacterial number is significantly lowered for 5 folds than that of wild-type locally injected with PBS.

| Groups | Number of samples | Mean number of bacteria (Mean ± SE, × 10⁶ CFU) |
|---|---|---|
| Plg+/+ with local injection of hPlg | 7 | 0.031 ± 0.011* |
| Plg+/+ with local injection of PBS | 7 | 0.14 ± 0.047 |

*$P < 0.05$, as compared to the group of Plg+/+ mice with local injection of PBS.

(Figure has same info as table, so it is not needed.)

Example 9

Supplementation of Plasminogen Restores/Enhances the Host Defense Against *S. Aureus*-Induced Periodontal Disease in Experimental Animals Methods The experimental model applied in this example is largely as described before (31), with necessary amendment to our research settings. Since *S. aureus* is one of the leading pathogen in periodontal disease, we will first use *S. aureus* as the infectious bacterium in this model. However, since we believe plasminogen plays a general role in potentiating the host defense against infection, depending on the laboratory conditions, we will probably use *P. gingivalis* as another infectious bacterium and perform similar studies as with *S. aureus*.

Thirty-six 8 week-old mice are randomly divided into three groups; ligature-infected, ligature-sham infected and controls. The mice are kept in conventional maintenance with a 12-hour light/12-hour dark cycle and are fed chow and water ad libitum.

*S. aureus*-adhered Ligatures for Oral Infection

For periodontal infection *S. aureus*-adhered ligatures are prepared by immersing 7 mm pieces of sterile ligature in LB broth and cultured at 37° C. to late logarithmic-early stationary phase. For sham group, the ligatures are processed with the above procedure but without the microorganisms. For enumeration of the bacteria on the ligatures it is suspended in 1 ml of LB broth and vortexed for 30 seconds. Thereafter the suspensions are diluted serially and spread on LB agar plates and incubated at 37° C. overnight. Viable bacterial colonies were then counted to evaluate the number of *S. aureus*.

Periodontal Infection

The infection of the periodontium in the experimental- and in the sham-infected groups are performed by placing and tying the ligatures around molar teeth in the maxilla of the anesthetized animals. A *S. aureus*-adhered- or a sham-treated ligature is tied on the first maxillary molar (M1) in the left maxilla with the help of sterile instruments. After the knot is tightened, the ligature is pushed into the crevice. Control animals are not ligated nor infected with the microorganism.

Detection and Identification of *S. aureus*

At the time of sacrifice, the presence of bacteria is examined by either taking the biofilm samples at the ligated molar area, or by pulling of the molar tooth carefully and in a sterile fashion. The samples are immediately transferred into LB broth, vigorously vortexed, serially diluted and placed onto LB agar plates and incubated at 37° C. overnight. The total CFU on the LB agar plates are counted thereafter to determine the number of bacteria.

Treatment with Plasminogen

After verification of the establishment of the model in mice, daily injection of human plg (10 ul/ul), either systemically through intravenous injection, or locally into the marginal gingiva at the left maxillary M1 will commence. The starting point of the injection may be at the time of experiment starts, or during the infectious stage of the experiment. At the end of the experiment, animals from each group will be sacrificed for final bacteriological sampling and analysis. The maxillary jaws separated from the cranium, de-fleshed from gross soft tissue such as tongue, and fixed in 4% paraformaldehyde (PFA) for 24 hours. Thereafter, samples were transferred to the decalcification solution to remove calcium from the bone tissue. After four weeks of decalcification process specimens were embedded in paraffin and sectioned at 5 µm thickness for morphological staining. Safranin 0 staining was used for morphological analysis, thus cartilage and mucin are stained in dark red, bone structures and teeth are blue, and the cell nuclei are stained dark blue.

Results

Based on our previous experience from plasminogen treatment of plg−/− mice, where injections both systemically and locally has reconstituted the gingival inflammation, the normal host defense (e.g. killing of bacteria) and proper periodontal re-attachment in these animals which have spontaneous periodontal disease, we strongly predict a similar response to the plasminogen treatment of plg−/− mice in the induced periodontal disease model as described above. Furthermore, based on the data of our previous study on another infection model, bacterial arthritis model, where local injection of plasminogen enhances the normal host defense against infectious bacteria in plg+/+ mice, we strongly predict that local treatment of plasminogen in plg+/+ mice during the induced periodontal disease model described above will also enhance the normal host defense in plg+/+ mice. And thus, all these data will show a strong indication that plasminogen is a novel drug candidate to preventing and treating periodontal disease, improving healing of periodontal wounds and promoting oral health

REFERENCE LIST

1. Clark, W. B., and Loe, H. 1993. Mechanisms of initiation and progression of periodontal disease. *Periodontol.* 2000. 2:72-82.
2. Liakoni, H., Barber, P., and Newman, H. N. 1987. Bacterial penetration of pocket soft tissues in chronic adult and juvenile periodontitis cases. An ultrastructural study. *J. Clin. Periodontol.* 14:22-28.
3. Branemark, P. I., Hansson, B. O., Adell, R., Breine, U., Lindstrom, J., Hallen, O., and Ohman, A. 1977. Osseointegrated implants in the treatment of the edentulous jaw. Experience from a 10-year period. *Scand. J. Plast. Reconstr. Surg. Suppl* 16:1-132.
4. Alexander C M, and Werb, Z. 1991. Extracellular matrix degradation. In *Cell Biology of Extracellular Matrix.* Hay ED, editor. Plenum Press. New York. 255-302.
5. Werb, Z., Mainardi, C. L., Vater, C. A., and Harris, E. D., Jr. 1977. Endogenous activiation of latent collagenase by rheumatoid synovial cells. Evidence for a role of plasminogen activator. *N. Engl. J. Med.* 296:1017-1023.
6. IIE, C. S., Wilhelm, S. M., Pentland, A. P., Marmer, B. L., Grant, G. A., Eisen, A. Z., and Goldberg, G. I. 1989. Tissue cooperation in a proteolytic cascade activating human interstitial collagenase. *Proc. Natl. Acad. Sci. U.S.A* 86:2632-2636.
7. Wiman, B., and Wallen, P. 1975. Structural relationship between "glutamic acid" and "lysine" forms of human plasminogen and their interaction with the NH2-terminal activation peptide as studied by affinity chromatography. *Eur. J. Biochem.* 50:489-494.
8. Saksela, O., and Rifkin, D. B. 1988. Cell-associated plasminogen activation: regulation and physiological functions. *Annu. Rev. Cell Biol.* 4:93-126.
9. Wallén P 1980. Biochemistry of plasminogen. In *Fibrinolysis.* Kline D L, and Reddy K N, editors. CRC press. Florida. 1-24.
10. Raum, D., Marcus, D., Alper, C. A., Levey, R., Taylor, P. D., and Starzl, T. E. 1980. Synthesis of human plasminogen by the liver. *Science* 208:1036-1037.
11. Sottrup-Jensen, L., Zajdel, M., Claeys, H., Petersen, T. E., and Magnusson, S. 1975. Amino-acid sequence of activation cleavage site in plasminogen: homology with "pro" part of prothrombin. *Proc. Natl. Acad. Sci. U.S.A* 72:2577-2581.
12. Collen, D., and Lijnen, H. R. 1991. Basic and clinical aspects of fibrinolysis and thrombolysis. *Blood* 78:3114-3124.
13. Alexander, C. M., and Werb, Z. 1989. Proteinases and extracellular matrix remodeling. *Curr. Opin. Cell Biol.* 1:974-982.
14. Mignatti, P., and Rifkin, D. B. 1993. Biology and biochemistry of proteinases in tumor invasion. *Physiol Rev.* 73:161-195.
15. Collen, D. 2001. Ham-Wasserman lecture: role of the plasminogen system in fibrin-homeostasis and tissue remodeling. *Hematology. (Am. Soc. Hematol. Educ. Program.)*1-9.
16. Rifkin, D. B., Moscatelli, D., Bizik, J., Quarto, N., Blei, F., Dennis, P., Flaumenhaft, R., and Mignatti, P. 1990. Growth factor control of extracellular proteolysis. *Cell Differ. Dev.* 32:313-318.
17. Andreascn, P. A., Kjoller, L., Christensen, L., and Duffy, M. J. 1997. The urokinase-type plasminogen activator system in cancer metastasis: a review. *Int. J. Cancer* 72:1-22.
18. Rifkin, D. B., Mazzieri, R., Munger, J. S., Noguera, T., and Sung, J. 1999. Proteolytic control of growth factor availability. *APMIS* 107:80-85.
19. Lahteenmaki, K., Kuusela, P., and Korhonen, T. K. 2001. Bacterial plasminogen activators and receptors. *FEMS Microbiol. Rev.* 25:531-552.
20. Broder, C. C., Lottenberg, R., von Mering, G. O., Johnston, K. H., and Boyle, M. D. 1991. Isolation of a prokaryotic plasmin receptor. Relationship to a plasminogen activator produced by the same micro-organism. *J. Biol. Chem.* 266:4922-4928.
21. Berge, A., and Sjobring, U. 1993. PAM, a novel plasminogen-binding protein from *Streptococcus pyogenes. J. Biol. Chem.* 268:25417-25424.
22. Fuchs, H., Simon, M. M., Wallich, R., Bechtel, M., and Kramer, M. D. 1996. *Borrelia burgdorferi* induces secretion of pro-urokinase-type plasminogen activator by human monocytes. *Infect. Immun.* 64:4307-4312.
23. Brandtzaeg, P., Joo, G. B., Brusletto, B., and Kierulf, P. 1990. Plasminogen activator inhibitor 1 and 2, alpha- 2-antiplasmin, plasminogen, and endotoxin levels in systemic meningococcal disease. *Thromb. Res.* 57:271-278.
24. Fuchs, H., Simon, M. M., Wallich, R., Bechtel, M., and Kramer, M. D. 1996. *Borrelia burgdorferi* induces secretion of pro-urokinase-type plasminogen activator by human monocytes. *Infect. Immun.* 64:4307-4312.
25. Klemm, P., and Schembri, M. A. 2000. Fimbriae-assisted bacterial surface display of heterologous peptides. *Int. J. Med. Microbiol.* 290:215-221.
26. Lahteenmaki, K., Westerlund, B., Kuusela, P., and Korhonen, T. K. 1993 Immobilization of plasminogen on *Escherichia coli* flagella. *FEMS Microbiol. Lett.* 106:309-314.
27. Berge, A., and Sjobring, U. 1993. PAM, a novel plasminogen-binding protein from *Streptococcus pyogenes*. *J. Biol. Chem.* 268:25417-25424.
28. Pancholi, V., and Fischetti, V. A. 1998. alpha-enolase, a novel strong plasmin(ogen) binding protein on the surface of pathogenic streptococci. *J. Biol. Chem.* 273: 14503-14515.
29. Harrington, D. J. 1996. Bacterial collagenases and collagen-degrading enzymes and their potential role in human disease. *Infect. Immun.* 64:1885-1891.
30. Paul, R., Lorenzl, S., Koedel, U., Sporer, B., Vogel, U., Frosch, M., and Pfister, H. W. 1998. Matrix metalloproteinases contribute to the blood-brain barrier disruption during bacterial meningitis. *Ann. Neurol.* 44:592-600.
31. Kimura, S., Nagai, A., Onitsuka, T., Koga, T., Fujiwara, T., Kaya, H., and Hamada, S. 2000. Induction of experimental periodontitis in mice with *Porphyromonas gingivalis*-adhered ligatures. *J. Periodontol.* 71:1167-1173.

The invention claimed is:

1. A method of treatment of infectious periodontal disease comprising:
    injecting a pharmaceutical composition comprising a compound, wherein the compound is human plasminogen, in an effective amount to a subject in need thereof,
        wherein the periodontal disease is, or is caused by, a bacterial infection and the pharmaceutical composition is in an amount effective to reduce the number of bacteria in the bacterial infection.
2. The method of claim 1, wherein the periodontal disease is selected from the group consisting of periodontitis, gingivitis, necrotizing gingivitis, periimplantitis, and peri-implant mucositis.
3. The method of claim 1, wherein the subject is a human.
4. The method of claim 1, wherein the subject is a non-human mammal.
5. The method of claim 1, wherein the pharmaceutical composition further comprises a pharmaceutically acceptable carrier.
6. The method of claim 1, wherein the pharmaceutical composition is selected from the group consisting of an aqueous solution and a gel.
7. The method of claim 1, wherein the pharmaceutical composition is administered by a method selected from the group consisting of local administration and systemic administration.
8. The method of claim 1, wherein the administering is repeated at least once.
9. The method of claim 8, wherein the administering is repeated daily.
10. The method of claim 1, further comprising a step selected from the group consisting of activating inflammatory cells, enhancing keratinocyte migration, reducing bacterial growth, removing necrotic tissue, improving tissue remodeling, and enhancing cytokine expression.
11. The method of claim 1, wherein the compound is in an amount of at least 10 mg/ml.
12. A method of promoting the healing of infectious periodontal wounds comprising:
    injecting a pharmaceutical composition comprising a compound, wherein the compound is human plasminogen, in an effective amount to a subject in need thereof,
    wherein the infectious bacterial periodontal wound is a wound caused by injury or a wound caused by periodontal surgery or plastic surgery and the pharmaceutical composition is in an amount effective to reduce the number of infectious bacteria in the infectious bacterial periodontal wound.
13. The method of claim 12, wherein the subject is a human.
14. The method of claim 12, wherein the subject is a non-human mammal.
15. The method of claim 12, wherein the pharmaceutical composition further comprises a pharmaceutically acceptable carrier.
16. The method of claim 12, wherein the pharmaceutical composition is selected from the group consisting of an aqueous solution and a gel.
17. The method of claim 12, wherein the pharmaceutical composition is administered by a method selected from the group consisting of local administration and systemic administration.
18. The method of claim 12, wherein the administering is repeated at least once.
19. The method of claim 18, wherein the administering is repeated daily.
20. The method of claim 12, further comprising a step selected from the group consisting of reducing fibrin deposition, promoting keratinocyte migration, enhancing cytokine expressions, removing necrotic tissue, activating inflammatory cells, and improving tissue remodeling.
21. The method of claim 12, wherein the compound is in an amount of at least 10 mg/ml.
22. A method of prophylaxis of infectious periodontal disease comprising:
    injecting a pharmaceutical composition comprising a compound, wherein the compound is human plasminogen, in an effective amount to a subject in need thereof,
    wherein the infectious periodontal disease is due to wounds caused by trauma or surgery, and wherein the infectious periodontal disease is caused by bacterial infection and the pharmaceutical composition is in an amount effective to reduce the number of bacteria of the bacterial infection.
23. The method of claim 22, wherein the infectious periodontal disease is periimplantitis or peri-implant mucositis.
24. The method of claim 22, wherein the subject is human.
25. The method of claim 22, wherein the subject is a non-human mammal.
26. The method of claim 22, wherein the pharmaceutical composition further comprises a pharmaceutically acceptable carrier.

27. The method of claim 22, wherein the pharmaceutical composition is selected from the group consisting of an aqueous solution and a gel.

28. The method of claim 22, wherein the pharmaceutical composition is administered by a method selected from the group consisting of local administration and systemic administration.

29. The method of claim 22, wherein the administering is repeated at least once.

30. The method of claim 29, wherein the administering is repeated daily.

31. The method of claim 22, further comprising a step selected from the group consisting of activating inflammatory cells, enhancing keratinocyte migration, reducing bacterial growth, removing necrotic tissue, improving tissue remodeling, and enhancing cytokine expression.

32. The method of claim 22, wherein the compound is in an amount of at least 10 mg/ml.

* * * * *